(12) United States Patent
Bauer

(10) Patent No.: US 9,801,832 B2
(45) Date of Patent: *Oct. 31, 2017

(54) PHARMACEUTICAL COMPOSITION HAVING SYNERGISTIC ACTION OF DIRECT CATALASE INHIBITORS AND MODULATORS OF NO METABOLISM OR OF EXTRACELLULAR SUPEROXIDE ANION PRODUCTION WHICH LEAD TO CATALASE DESTRUCTION

(71) Applicant: Universitaetsklinikum Freiburg, Freiburg (DE)

(72) Inventor: Georg Bauer, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/410,221

(22) PCT Filed: Jun. 20, 2013

(86) PCT No.: PCT/EP2013/062822
§ 371 (c)(1),
(2) Date: Dec. 22, 2014

(87) PCT Pub. No.: WO2014/001183
PCT Pub. Date: Jan. 3, 2014

(65) Prior Publication Data
US 2015/0335663 A1 Nov. 26, 2015

(30) Foreign Application Priority Data
Jun. 26, 2012 (EP) .................... 12173548

(51) Int. Cl.
| | | |
|---|---|---|
| A61K 31/60 | (2006.01) | |
| A61K 31/352 | (2006.01) | |
| C07K 16/40 | (2006.01) | |
| A61K 31/337 | (2006.01) | |
| A61K 31/105 | (2006.01) | |
| A61K 31/05 | (2006.01) | |
| A61K 31/496 | (2006.01) | |
| A61K 31/4164 | (2006.01) | |
| A61K 31/26 | (2006.01) | |
| A61K 31/198 | (2006.01) | |
| A61K 31/375 | (2006.01) | |
| A61K 31/519 | (2006.01) | |
| A61K 31/10 | (2006.01) | |
| A61K 31/366 | (2006.01) | |
| A61K 31/4196 | (2006.01) | |
| A61K 31/426 | (2006.01) | |
| A61K 31/427 | (2006.01) | |
| A61K 31/69 | (2006.01) | |

(52) U.S. Cl.
CPC .............. *A61K 31/05* (2013.01); *A61K 31/10* (2013.01); *A61K 31/105* (2013.01); *A61K 31/198* (2013.01); *A61K 31/26* (2013.01); *A61K 31/337* (2013.01); *A61K 31/352* (2013.01); *A61K 31/366* (2013.01); *A61K 31/375* (2013.01); *A61K 31/4164* (2013.01); *A61K 31/4196* (2013.01); *A61K 31/426* (2013.01); *A61K 31/427* (2013.01); *A61K 31/496* (2013.01); *A61K 31/519* (2013.01); *A61K 31/60* (2013.01); *A61K 31/69* (2013.01); *C07K 16/40* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2006/0172012 A1 | 8/2006 | Finley et al. | |
| 2007/0292355 A1* | 12/2007 | Tamarkin ................ | A61K 9/12 424/43 |
| 2008/0038367 A1 | 2/2008 | Saloum | |

FOREIGN PATENT DOCUMENTS

| | | |
|---|---|---|
| EP | 0 349 113 A1 | 1/1990 |
| WO | WO 2006/017559 | 2/2006 |
| WO | WO 2008/071242 | 6/2008 |
| WO | WO 2012/022659 | 2/2012 |
| WO | WO 2012/080518 | 6/2012 |
| WO | WO 2012/172034 | 12/2012 |

OTHER PUBLICATIONS

Wu et al. Apoptosis (2007) 12:593-612.*
Abdelmagid et al. Journal of Cellular Biochemistry 112:1084-1092 (2011).*
Chang et al. Cancer 1996 77 (1) 14-18.*
Tanaka et al. European Journal of Cancer (32a) 1996, 226-230.*
Poncet et al. American Journal of Clinical Oncology. 2009 32(1):98;.*
Faltus et al. Neoplasia 2004 (6) 786-795;.*
Bullock et al. The Oncologist 2008; 13:515-525.*
Bechtel, Wibke et al., *Anticancer Research Greece*, Nov. 2009, vol. 29, No. 11, pp. 4541-4557.
Heinzelmann, Sonja et al., *Biological Chemistry*, Jun. 2010, vol. 391, No. 6, pp. 675-693.
Juarez, Jose C et al., *Clinical Cancer Research* (JAACR), Aug. 2006, vol. 12, No. 16, pp. 4974-4982.
Olas, B. et al., *ACTA Biochimica Polonica*, Nov. 1999, vol. 46, No. 4, pp. 961-966.
Ward, Roberta J. et al., *Alcohol and Alcoholism*, Jan. 2001, vol. 36, No. 1, pp. 39-43.
Wiemer, E. A. C. et al., *Journal of Immunological Methods*, Jul. 1992, vol. 151, No. 1-2, pp. 165-175.
Yen, Gow-Chin et al., *Free Radical Research*, May 2003, vol. 37, No. 5, pp. 509-514.

* cited by examiner

*Primary Examiner* — Jeffrey S Lundgren
*Assistant Examiner* — Michael Schmitt
(74) *Attorney, Agent, or Firm* — Chalin A. Smith; Smith Patent, LLC

(57) ABSTRACT

The present patent application relates to a pharmaceutical composition, characterized in that it comprises at least one active ingredient which can bring about a singlet oxygen-independent direct catalase inactivation and that the composition further comprises at least one active ingredient that leads to inactivation of catalase as a result of modulation of the nitrogen oxide or superoxide anion metabolism of the cells and subsequent singlet oxygen formation.

7 Claims, 29 Drawing Sheets

PHARMACEUTICAL COMPOSITION HAVING SYNERGISTIC ACTION OF DIRECT CATALASE INHIBITORS AND MODULATORS OF NO METABOLISM OR OF EXTRACELLULAR SUPEROXIDE ANION PRODUCTION WHICH LEAD TO CATALASE DESTRUCTION

PRIORITY

This application corresponds to the national phase of International Application No. PCT/EP2013/062822, filed Jun. 20, 2013, which, in turn, claims priority to European Patent Application No. 12.173548.4 filed Jun. 26, 2012, the contents of which are incorporated by reference herein in their entirety.

STATE OF THE ART

Bechtel and Bauer, *Anticancer Res.* 29: 4541-4558 (2009) present a basic phenomenon: Inhibition of catalase by 3-aminotriazole results in that tumor cells that neither autocrine nor by interaction with non-transformed cells (spatially separated by means of a separating chamber system) go to ROS signaling-mediated apoptosis become sensitive for these two processes. Here, by the use of inhibitors it is ensured that after the action of the catalase inhibitor there actually run the same ROS-mediated signal paths as in transformed cells that are not protected by catalase and that represent the precursors of tumor cells. The publication also shows clearly that non-transformed cells that have no activated NADPH oxidase in the cell membrane also after administration of the catalase inhibitor do not go to apoptosis. Thus, the publication differentiates between normal cells insensitive for ROS signaling, sensitive transformed cells, and resistant tumor cells that can be transferred to the sensitive state by catalase inhibition.

Heinzelmann and Bauer, *Biol. Chem.* 391 (2010): 675-693 broaden the concepts presented in the work of Bechtel and Bauer, 2009: At first, by the apoptosis-triggering action of effective antibodies against catalase that are not cell-permeable, by fluorescent staining of the catalase on living cells, and by the use of peroxynitrite it is shown that the catalase that is important for the protection of the tumor cells is externally located on the cell membrane. It is further shown that in gradual catalase inhibition in gastric carcinoma cells at first the NO/peroxynitrite path is reactivated and then, with a stronger inhibition of the catalase is replaced by the HOCl signal path. This publication also shows for the first time that in certain tumor systems (e.g. Ewing's sarcoma and neuroblastoma) intercellular signaling exclusively runs via the NO/peroxynitrite path. Moreover, the work shows that NO and $H_2O_2$ negatively influence each other via a complex consumption reaction and that in this way the quality of the intercellular ROS signaling can be modulated. A central point is to demonstrate that the unexpected protective action of the membranous catalase against the NO/peroxynitrite path (that complements the known effect on the HOCl path) is actually achieved by a direct degradation of peroxynitrite, wherein the central intermediate of the catalase action, compound I (CAT $Fe^{IV}=O^{+\cdot}$), could actually be biochemically detected. Finally, the gradual protection of ROS sensitive transformed cells by increasing concentrations of exogenously added soluble catalase confirmed the correctness of the conclusion that catalase is sufficient for the protection of tumor cells from ROS signaling. Although, in this publication the interplay between NO/peroxynitrite and catalase as well as between NO and $H_2O_2$ was analyzed in many ways, no indication to synergy effects can be derived from the findings obtained and the formulated biochemical/cell-biological concepts. Thus, this work does not anticipate the object of the application.

Olas et al., *Acta Biochem. Polonica* 46: 961-966, 1999 show that resveratrol in thrombocytes leads to a reduction of the production of superoxide anions, hydrogen peroxide, and singlet oxygen. A minor increase of the superoxide anion production at lower concentrations of resveratrol (6.25 and 12.5 µg/ml) has proven to be statistically insignificant, as the authors emphasize. These findings stand in direct contrast to the findings obtained for tumor cells that are published somewhere else (WO 2012/022659). There, it is shown that resveratrol in tumor cells leads to a dramatic increase of the superoxide anion production.

Wiemer et al., *J. Immunol. Methods* 151:165-175 (1992) presents several hybridoma clones the monoclonal antibodies of which bind to native or denaturized catalase. That is, this work characterizes the bondability of various antibodies to catalase without obtaining data including the effect on the enzyme activity of the catalase. The data obtained here are necessary for future use of these immunological tools, but they have no connection with the biological function of tumor cell-specific catalase. From the work of Wiemer et al., 1992 no predictions about the sensitization of tumor cells for ROS signaling and, in particular not about the presently disclosed complex synergy effects can be made.

Yen et al., *Free Rad. Res.* 37: 509-514 (2003) shows the anti-oxidative effect of resveratrol and the resulting protection of DNA from the effect of reactive oxygen species, such as e.g. hydrogen peroxide. This uncontested effect of resveratrol has no connection with the effect of resveratrol relevant for the present application in combination with direct catalase inhibitors, namely the ROS-mediated induction of apoptosis that is based on a pro-oxidative effect. It could even be concluded that resveratrol ought to inhibit ROS signaling due to its anti-oxidative potential.

US 2006/172012 of Finley relates to the anti-inflammatory effect of several natural substances. From this application no predictions can be made about the anti-tumor effect of the mentioned active ingredients. Since in the patent application of Finley et al. no biochemical basics for the claimed effects are shown or mentioned, it remains unclear whether the mentioned single active ingredients or their combinations would selectively have an inhibiting or increasing or even no effect on the presently disclosed synergy effects in the ROS-mediated induction of apoptosis in tumor cells. From the effect of these substances on inflammation processes speculatively also no rationally justified prediction can be made about their effect with tumor cells.

US 2008/0038367 presents several combinations of natural substances as nutrient supplements. Here, there is no relation to the effect of these substances on existing tumors, no indication on synergy effects between such substances with respect to the induction of apoptosis in tumors, and no relation to the effect on tumor-protective catalase. That is, from this application no predictions can be derived that relate to the present application.

WO 2008/071242 is based on the potential of NO to permit formation of singlet oxygen via a reversible inhibition of the tumor-protective catalase, wherein several complex amplification steps are required. As a consequence, finally tumor cell catalase itself is destroyed by singlet oxygen (possibly by reaction of singlet oxygen with a histidine residue in the active center) and subsequently ROS signaling and thereby triggered apoptosis is enabled. WO 2008/071242 in no way anticipates the present teaching. Since the effect of the NO modulators in the singlet oxygen-mediated induction of apoptosis is based on the destruction of catalase it would only be possible to predict that an additional catalase inhibition could lead to an additive enhancing effect. However, a synergistic effect, as presently explained, could not be predicted. Such an effect is unexpected and surprising.

To the statement of the application WO 2008/071242 WO 2012/022659 adds the finding that the simultaneous application of stimulators of the NADPH oxidase and inhibitors of the NO dioxygenase results in a synergistic effect on the singlet oxygen-dependent destruction of the catalase. This results in a corresponding downstream effect on the ROS-mediated induction of apoptosis in the tumor cells. However, a synergistic effect, as explained in the present application, cannot be predicted. Such an effect is surprising.

BACKGROUND OF THE PRESENT INVENTION

Malignant cells are characterized by the extracellular production of superoxide anions by membranous NADPH oxidase (NOX-1). Here, the activity of NOX is controlled by oncogenes such as e.g., RAS by involving RAC. The superoxide anions generated by malignant cells and their dismutation product hydrogen peroxide are essential for the proliferation of these cells and for the maintenance of their transformed state (summarized in Heinzelmann and Bauer, [2010], Biol. Chem., Vol. 391, pp. 675-693). However, the other side of the coin from the extracellular production of reactive oxygen species (ROS) is the formation of intercellular ROS-mediated signal paths selectively directing against cells with the transformed phenotype. These are the main paths shown in FIG. 1, namely the HOCl and the NO/peroxynitrite signal path as well as two further paths of secondary importance, namely the nitryl chloride path and the metal catalyzed Haber-Weiss reaction that are not considered in FIG. 1. In the course of the tumor progression tumor cells acquire resistance against the intercellular ROS signal paths by expressing catalase (CAT) on their cell membrane. This inhibits the HOCl and the nitryl chloride path as well as the metal catalyzed Haber-Weiss reaction by converting hydrogen peroxide into water and oxygen, and counteracts the NO/peroxynitrite path by decomposing peroxynitrite and oxidizing NO to $NO_2$ with the help of its active intermediate CAT $Fe^{IV}=O^+$ (compound I), and so prevents the formation of peroxynitrite. Cancelling the catalase (CAT) mediated protection of tumor cells represents an attractive concept for the development of a novel form of tumor therapy that is specifically directed against cells with the malignant phenotype (due to the features of membranous catalase and superoxide anion production) and does not endanger normal cells, since these neither produce extracellular superoxide anions nor express membranous catalase.

The procedure disclosed in DE 103 58 077 A1 2005.07.28 permits search for active ingredients that specifically and directly inhibit membranous catalase and thus, reactivate intercellular ROS signal paths which then induce apoptosis in tumor cells. FIG. 2 schematically shows the ROS (reactive oxygen species) controlled induction of apoptosis that is reactivated by the inhibition of the catalase.

The same selective induction of apoptosis in tumor cells can be achieved when extracellular singlet oxygen is formed (for example by exposure of the photosensitizer photofrin to light) which then reacts with a histidine residue in the catalase and thus, inactivates it. This is schematically illustrated in FIG. 3.

However, formation of singlet oxygen can also be achieved by modulation of the NO metabolism of the cells. This is schematically illustrated in FIG. 4. Inhibition of cellular arginase (1), addition of arginine, inhibition of the NO dioxygenase (NOD) (2) or the associated cytochrome P450-dependent oxidoreductase (POR) (3) lead to a sharp increase in the available NO concentration. Finally, by complex amplification steps this results in the formation of extracellular singlet oxygen that inactivates catalase. In EPA 07.870201.6 there is disclosed a method for identifying compounds that induce tumor apoptosis by inactivation of catalase on the surface of tumor cells.

Further, it was described that by manipulation of the NO metabolism and the simultaneous enhancement of the NOX activity a remarkable synergistic effect can be achieved that leads to a reduction of the required concentrations of the single active substance. This mechanism of action is schematically illustrated in FIG. 5. Making use of the synergistic effect between modulators of the NO and der NADPH oxidase is disclosed in EP 10173500.9 A.

While the above-explained synergy mechanisms always act on different partial paths of the ROS signal paths the present invention relates to the synergistic interaction between one or two partial paths of the ROS signaling and a sub-toxic inhibition of the catalase. These combinations then in total lead to a massive inactivation of the catalase and the subsequent selective cell death of the tumor cells.

SUMMARY OF THE PRESENT INVENTION

The present invention is based on the unexpected finding that the combination of direct inhibitors of the catalase with modulators of the NO or superoxide anion metabolism, that at first form singlet oxygen and subsequently irreversibly inactivate catalase, leads to a strong synergistic effect in the selective induction of apoptosis in tumor cells. Here, by the combination of at least one active ingredient of the group of direct catalase inhibitors with at least one active ingredient of the group of modulators of the NO or superoxide anion metabolism a marked and selective induction of apoptosis in tumor cells can be achieved, although the use of the respective active ingredients alone in the same concentration range does not lead to a perceptible induction of apoptosis.

This finding is unexpected because it had to be assumed on the basis of the current state of knowledge that the action of direct catalase inhibitors and such active ingredients that lead to a singlet oxygen-dependent catalase destruction via the modulation of the NO or superoxide anion metabolism could be complementary in their action only in an additive manner.

DETAILED DESCRIPTION OF PREFERRED EMBODIMENTS OF THE INVENTION

On the basis of these findings, a specific form of the synergistic anti-tumor effect by means of induction of apoptosis is disclosed.

DEFINITION OF TERMS

A) Direct Catalase Inhibitors: active ingredients immediately leading to an inhibition of the catalase, preferably the protective catalase that is externally located on the membrane of tumor cells. The effect of this group of catalase inhibitors does not require the formation of singlet oxygen. The consequence of the catalase inhibition is selective induction of apoptosis in tumor cells that is controlled and caused by intercellular ROS signaling. Among "direct catalase inhibitors" in this sense in addition to antibodies against catalase in the wider sense there are preferably antibodies against SOD, since after inhibition of the tumor cell SOD due to the increase of the free superoxide anion concentration there is inevitably an inhibition of catalase. No singlet oxygen is involved in this process. Preferred examples for "direct catalase inhibitors" are: 3-aminotriazole, antibodies against catalase and against SOD, salicylic acid, ascorbic acid, and methyldopa. Direct catalase inhibition with relevance to the induction of apoptosis in tumor cells can be determined by pre-incubating tumor cells at first in the presence of the singlet oxygen scavenger histidine (2 mM) with the substance to be tested in increasing concentration (between 10 and 30 minutes at 37° C.) and subsequently adding peroxynitrite in the concentration range between 10 and 200 µM. The tumor cells are protected from the apoptosis-triggering effect of peroxynitrite by their membranous catalase. An inhibition of the catalase partially or completely cancels this protection and in the presence of peroxynitrite leads to the induction of apoptosis. The presence of 2 mM histidine ensures that the measured induction of apoptosis is not a singlet oxygen-mediated inactivation of the catalase by destruction of its active center. Alternatively, instead of addition of histidine inhibition of the NADPH oxidase by 100 µM AEBSF may take place. With prevented superoxide anion production also no singlet oxygen formation in the test system is possible.

B) Modulators of the NO or superoxide anion metabolism that lead to an inactivation of the catalase: This group of active ingredients by an increase of the available NO concentration or by an increase of the superoxide anion production through several biochemically defined steps leads to the formation of singlet oxygen that inactivates the catalase by reaction with the histidine in the active center of the catalase and thus, enables intercellular ROS signaling. Examples of modulators of the NO metabolism are arginine, arginase inhibitors such as e.g. Nor-NOHA, inhibitors of the NO dioxygenase (NOD) such as e.g. flavonoids, taxol, epothilon B, anthocyans, artemisinin, azoles, diallyldisulfide, palmitic acid, and inducers of the NOS expression such as e.g. interferon γ. Examples of modulators of the superoxide anion production by stimulation of NOX-1 are resveratrol, transforming growth factor-beta.

The experimental results that have led to the present invention are disclosed in the following in the form of FIG. 6 and following as well as the detailed legend to those figures.

List of abbreviations used in the experiments and figures, respectively

AEBSF 4-(2-aminoethyl)-benzenesulfonyl fluoride (inhibitor of the NADPH oxidase)
ABH 4-aminobenzoyl hydrazide (peroxidase inhibitor)
3-AT 3-aminotriazole (catalase inhibitor)
aCAT antibody against catalase; a monoclonal antibody (mouse; IgG1) against human catalase (Clone CAT-505) (batch number: 088K4809), manufacturer Sigma Aldrich, Schnelldorf, Germany, was preferably used.
aSOD antibody against SOD; a monoclonal antibody (mouse, IgG1) against human SOD-1 (Clone SD-G6) (batch number 035K4823), manufacturer Sigma Aldrich, Schnelldorf, Germany, was preferably used.
CAT catalase
Compound I activated intermediate stage of catalase of formula CAT $Fe^{IV}=O^{+\cdot}$. Compound I is formed in the reaction of catalase with a molecule hydrogen peroxide or peroxynitrite.
DEA NONOate 2-(N,N-diethylamino)-diazenolate-2-oxide. diethylammonium salt (rapidly decomposing NO donor)
Duox dual oxidase (membranous enzyme consisting of an NADPH oxidase and a peroxidase domain. The peroxidase domain is cleaved off with the help of proteases.)
FBS fetal bovine serum
FeTPPS 5-, 10-, 15-, 20-tetrakis(4-sulfonatophenyl)porphyrinato iron(III) chloride (peroxynitrite decomposition catalyst)
MnTE-2PyP Mn(III) meso-tetrakis(N-ethyl-2-pyridyl)porphyrin pentachloride (cell-permeable SOD mimetic)
L-NAME N-ω-nitro-L-arginine methylester hydrochloride (NOS inhibitor)
NO nitric oxide
NOD nitric oxide dioxygenase (oxidizes NO to nitrate)
NOS NO synthase
NOX NADPH oxidase (here, in particular the membranous NOX-1)
POD peroxidase; in this context in particular the ability of certain peroxidases takes effect that in the presence of hydrogen peroxide they are able to oxidize chloride to HOCl
PON peroxynitrite
POR cytochrome P 450 oxidoreductase
RAS, RAC oncogenes
ROS reactive oxygen and nitrogen species; radical and non-radical species such as superoxide anions, hydroxyl radicals, nitric oxide, hydrogen peroxide, HOCl, peroxynitrite, etc.
siRNA small interfering RNA; reagent to specifically downregulate the synthesis of defined gene products
SOD superoxide dismutase; preferably SOD-1 ($Cu^{++}$ in the active center of the tumor cells and MnSOD from bacteria for analytical purposes)
TGF-beta transforming growth factor type beta Object of the present invention are pharmaceutical compositions that are characterized in that on the one hand they comprise at least one active ingredient which can bring about a singlet oxygen-independent direct catalase inactivation. In addition, these compositions comprise at least one further active ingredient that leads to inactivation of catalase as a result of modulation of the nitrogen oxide or superoxide anion metabolism of the cells and subsequent singlet oxygen formation.

In a preferred embodiment, the active ingredient that is capable of singlet oxygen-independent direct inactivation of the catalase is antibodies against superoxide dismutase as well as antibodies against catalase. The production of such antibodies is well known to the skilled person. Preferably, these are monoclonal, humanized, or human antibodies that specifically bind to epitopes of the human catalase or the human superoxide dismutase that is preferably present on the surfaces of cells, in particular of tumor cells. Other examples of suitable active ingredients are salicylic acid and derivatives derived therefrom, ascorbic acid, and methyldopa.

The other active ingredient that is present in the pharmaceutical compositions according to the invention are active ingredients that lead to inactivation of catalase as a result of modulation of the nitrogen oxide or superoxide anion metabolism of the cells and subsequent singlet oxygen formation. These active ingredients are preferably selected from the group of substances that can increase the available nitrogen oxide concentration in cells. In a particularly preferred embodiment, the active ingredient that leads to inactivation of catalase as a result of modulation of the nitrogen oxide or superoxide anion metabolism of the cells and subsequent singlet oxygen formation are compounds that are selected from compounds of the groups flavonoids, anthocyanes, taxol, epothilon B, artemisin, diallyldisulfide, Nor-NOHA, 2(S)amino-6-boronohexanoic acid.$NH_4$ (A-6-BHA), (2S)-(+)-amino-5-iodoacetamidopentanoic acid (A-5-IAAPA), S-(2-boronoethyl)-L-cysteine.$NH_4$ (BEC), $N^G$-hydroxy-L-arginine.monoacetate ("NOHA"), azoles (such as e.g. itraconazole, econazole, fluconazole, miconazole, ketoconazole), isothiocyanates such as e.g. methylisothiocyanate, allylisothiocyanate, and sulforaphane.

In a preferred embodiment, a pharmaceutical composition according to the invention comprises at least one active ingredient that can bring about a singlet oxygen-independent direct catalase inactivation, wherein this is selected from human or humanized antibodies against membranous human superoxide dismutase or human or humanized antibodies against human catalase. The active ingredient that leads to inactivation of catalase as a result of modulation of the nitrogen oxide or superoxide anion metabolism of the cells and subsequent singlet oxygen formation is selected from taxol, an anthocyane, or diallyldisulfide.

In a particularly preferred embodiment, the pharmaceutical composition comprises a human or humanized antibody against membranous human superoxide dismutase and taxol.

In a further particularly preferred embodiment, the pharmaceutical composition comprises a human or humanized antibody against membranous human superoxide dismutase and anthocyane.

In a further particularly preferred embodiment, the pharmaceutical composition comprises a human or humanized antibody against membranous human superoxide dismutase and diallyldisulfide.

In a further particularly preferred embodiment, the pharmaceutical compositions according to the invention can further contain resveratrol.

The respective active ingredients are used in the pharmaceutical compositions according to the invention in such concentrations that a sufficient concentration can be achieved at the respective tumor cells. The actually used concentrations depend on whether these are pharmaceutical compositions that are orally administered, or compositions that are parenterally administered such as injection solutions, infusions, and the like.

The pharmaceutical compositions according to the invention are preferably used to treat tumor diseases. The tumor diseases that can be treated with the compositions according to the invention preferably are types of tumors that in sufficient concentration provide the signal molecules that are required for catalase destruction under in vivo conditions. Preferably, the tumor diseases are selected from gastric carcinoma or lymphoma.

BRIEF DESCRIPTION OF THE FIGURES

The following explanation of the figures describes the present invention.

FIG. 1—Tumor cells are protected by membranous catalase from intercellular ROS signaling The illustration on the left shows the intercellular, on the right the intracellular area of a tumor cell and between them the potential intercellular ROS signaling. In the cell membrane there is the activated NADPH oxidase NOX-1 that generates superoxide anions extracellulary. These spontaneously dismutate to hydrogen peroxide and oxygen. The cells release peroxidase (POD) that is encoded by DUOX (not shown) and cleaved off by matrix metalloproteases. Hydrogen peroxide and chloride ions are converted by the free peroxidase (POD) to HOCl that reacts with superoxide anions to apoptosis-inducing hydroxyl radicals. With a relative excess of hydrogen peroxide the consumption reaction of HOCl occurs that weakens the HOCl path. NO synthase (NOS) generates NO that is either consumed by hydrogen peroxide in a complex consumption reaction or reacts with superoxide anions to peroxynitrite. After the formation of peroxynitrite acid and its decomposition into hydroxyl radicals and $NO_2$ the induction of apoptosis occurs. The two secondary signal paths nitryl chloride pathway and metal catalyzed Haber-Weiss reaction are not considered in the scheme.

It is particularly noted that the target cell function "formation of superoxide anions" is strictly associated with the transformed phenotype and is highly selective since it is controlled by activated oncogenes. However, the effector functions "release of peroxidase" and "NO release" can be performed both by not-transformed and transformed cells themselves. That's why intercellular ROS signaling goes both in the interaction between transformed and not-transformed cells (classical intercellular induction of apoptosis) and also in an autocrine manner between transformed cells.

Tumor cells on their outer surface bear sufficient membranous catalase (CAT) that destroys hydrogen peroxide and thus inhibits the HOCl path (as well as the not shown nitryl chloride path and the metal catalyzed Haber-Weiss reaction). Moreover, catalase also destroys peroxynitrite and thus effectively interferes with the NO/peroxynitrite path. For reasons of clarity, a second negative interaction of the catalase with the NO/peroxynitrite path is not shown: Compound I of the catalase can oxidize NO to $NO_2$ and thus inhibit the NO/peroxynitrite path.

Figure 1:
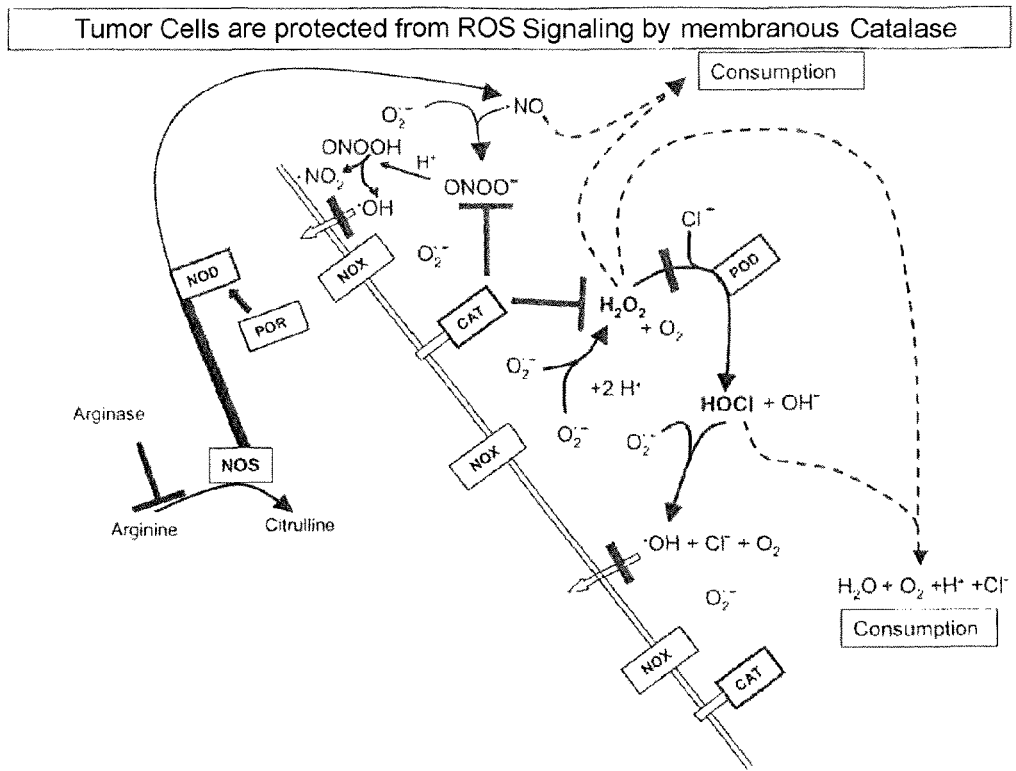
FIGS. 1-5 represent the interaction of the individual components underlying the present invention. Further, experiments were performed and the results of the experiments are given in FIGS. 6-29.
Figure 2:
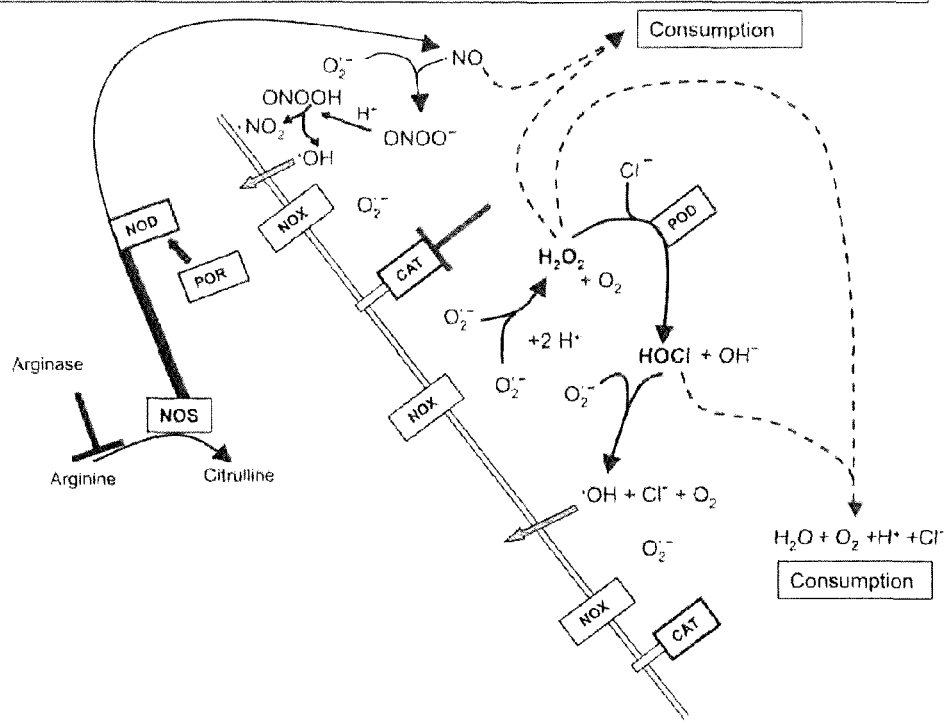

FIG. 2—Direct inhibition of protective catalase leads to the selective cell death of tumor cells Induction of apoptosis by ROS signaling can take place in tumor cells by direct inhibition of the catalase. DE 103 58 077 discloses methods that permit search for catalase inhibitors.

Figure 3:
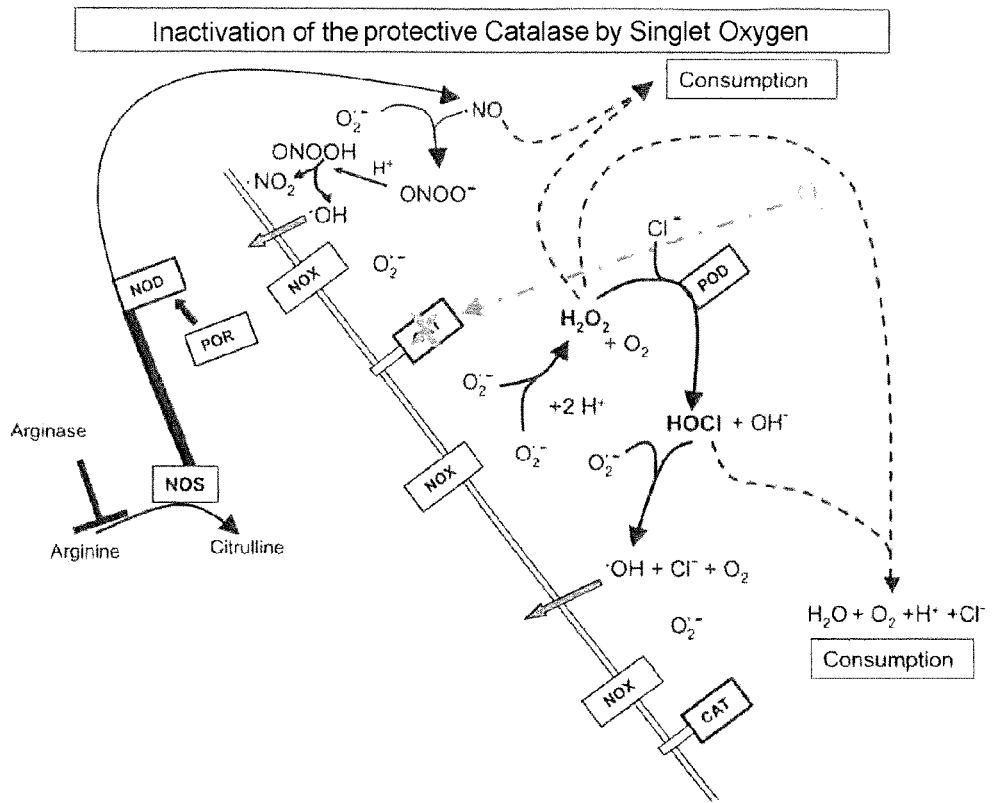

FIG. 3—Destruction of the catalase by exogenous singlet oxygen

ROS signaling can be reactivated by direct application of singlet oxygen generators (such as e.g. photofrin). Singlet oxygen reacts with histidine of the active center of the catalase and thus, leads to its inactivation.

Figure 4:
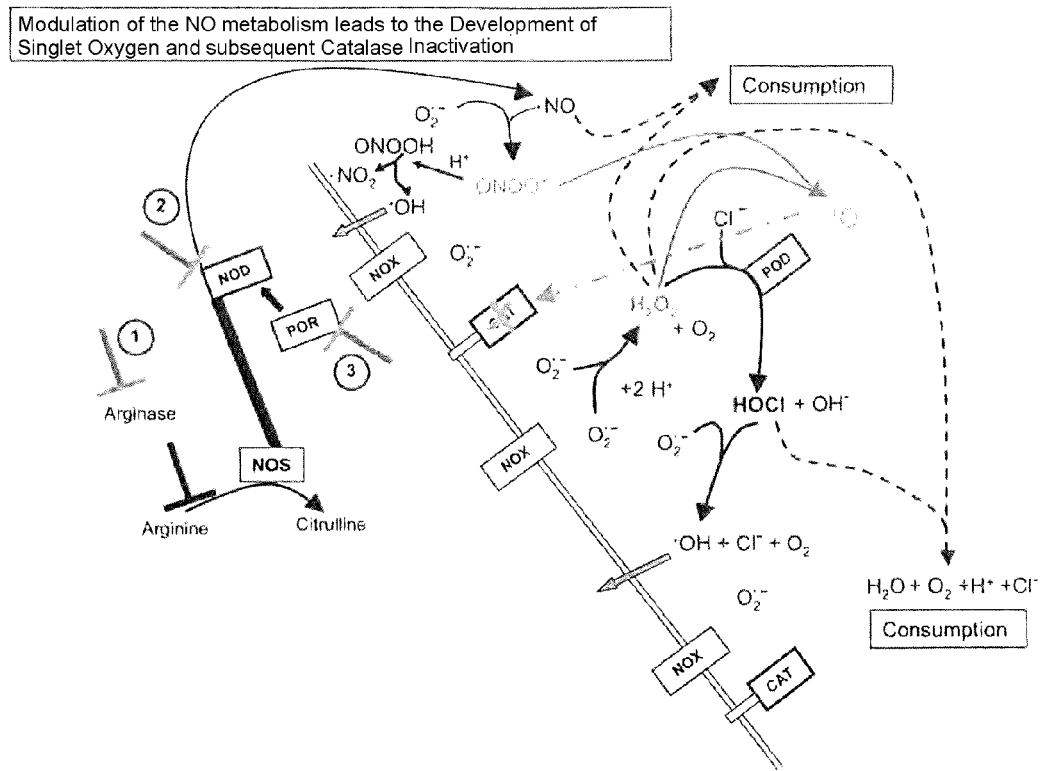

FIG. 4—Modulation of the NO metabolism leads to singlet oxygen-mediated catalase inactivation Modulation of the NO metabolism after several intermediate steps causes formation of singlet oxygen, catalase inactivation, and apoptosis (PCT/EP2007/006964). The increase in the available NO concentration leads to a reversible inhibition of the catalase. Now, this enables unreacted peroxynitrite and hydrogen peroxide to react with each other and thus, form singlet oxygen. Now this can ligand-independently activate the FAS receptor what inter alia leads to an increase in the NOX-1 activity. This inevitably results in an increase in the hydrogen peroxide concentration, which in turn enables the formation of new singlet oxygen and the destruction of further catalase molecules.

Figure 5:
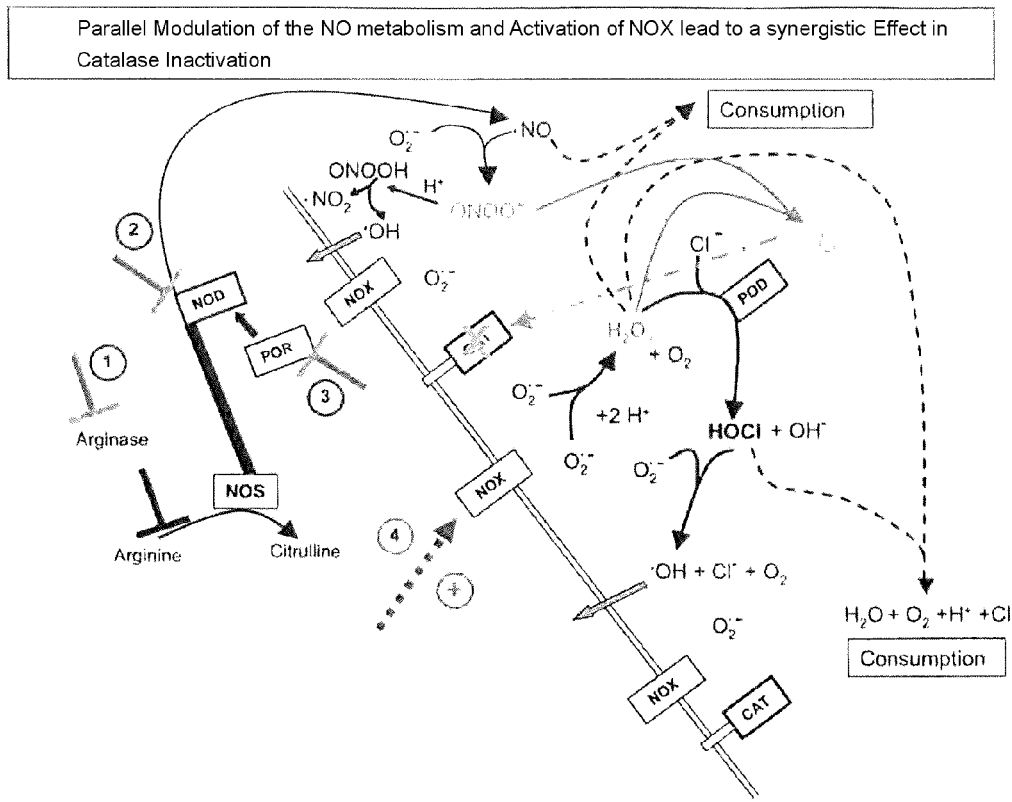

FIG. 5—Synergistic effects between NOX stimulators and modulators of the NO metabolism With the combination of NOX stimulators and modulators of the NO metabolism synergistic effects can be achieved (EPA 10173500.9). This can be explained by the fact that the parallel increase of the NO concentration and the superoxide anion production makes the FAS receptor-dependent amplification step unnecessary and thus, simplifies and enhances the overall process.

Figure 6:
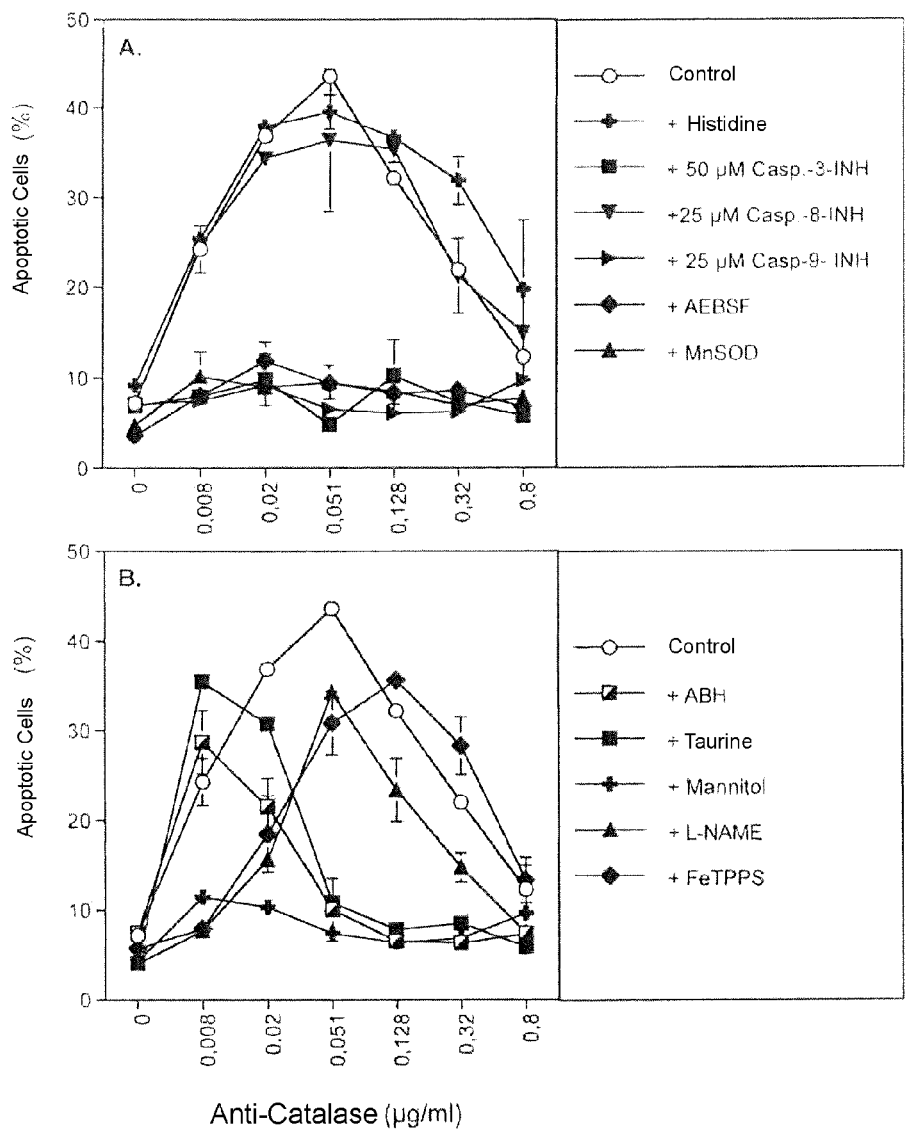

FIG. 6—Signal chemistry after inhibition of the tumor cell catalase by means of monoclonal antibodies against catalase 12 500 MKN-45 gastric carcinoma cells in 100 µl complete medium either remained untreated (control) or received 2 mM histidine (singlet oxygen scavenger), 50 µM Caspase-3 inhibitor, 25 µM Caspase-8 inhibitor, 25 µM Caspase-9 inhibitor, 100 µM AEBSF (NADPH oxidase inhibitor), 100 U/ml MnSOD (superoxide anion scavenger), 150 µM ABH (peroxidase inhibitor), 50 mM taurin (HOCl scavenger), 10 mM mannitol (hydroxyl free-radical scavenger), 2.4 mM L-NAME (NOS inhibitor), or 40 µM FeTPPS (peroxynitrite decomposer). Subsequently, the given concentrations of monoclonal antibodies against human catalase were added. After four hours of incubation at 37° C. the percentages of apoptotic cells were determined in duplicate batches according to the classical apoptosis features nuclear condensation, nuclear fragmentation, and membrane blebbing. Here, at least 200 cells were evaluated per batch. Control batches with control IgG instead of monoclonal antibody against catalase were also made and exhibited no induction of apoptosis (data not shown).

Application of monoclonal antibody against catalase (but not control antibodies) results in induction of apoptosis in the form of an optimum curve. Induction of apoptosis is independent of singlet oxygen (no inhibition by histidine), Caspase-8, but dependent on Caspase-9 and Caspase-3. The reaction depends on superoxide anions in the whole concentration range since an inhibitor of both the NADPH oxidase (AEBSF) and SOD leads to the arrest of the reaction. In the lower concentration range inhibitors of the NO/peroxynitrite path such as L-NAME (NOS inhibitor) and FeTPPS (peroxynitrite scavenger) inhibit. In the higher concentration range the reaction depends on HOCl (inhibitability by the HOCl scavenger taurine and the peroxidase inhibitor ABH). The inhibitability by the hydroxyl radical scavenger mannitol proves the central role of the apoptosis inductor hydroxyl radical that can evolve after decomposition of peroxynitrite acid and after interaction of HOCl with superoxide anions.

Figure 7:
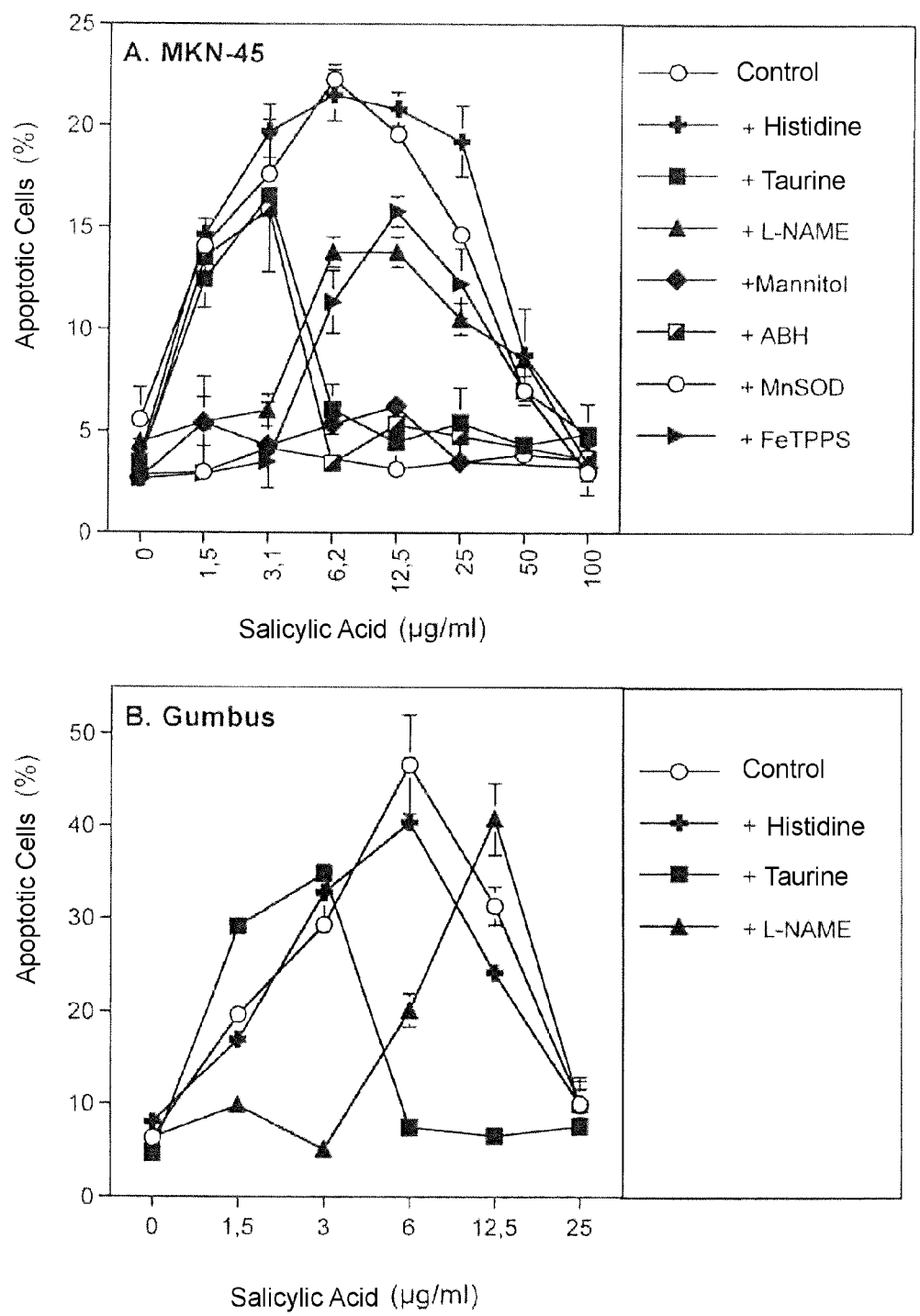

FIG. 7—Inhibition of the catalase by salicylic acid in MKN-45- or Gumbus cells (human lymphoma line) does not depend on singlet oxygen and exhibits the same inhibitor profile as the induction of apoptosis by anti-CAT 12 500 MKN-45 gastric carcinoma cells (A) or 25 000 Gumbus lymphoma cells (B) in 100 µl complete medium each either remained untreated (control) or received 2 mM histidine (singlet oxygen scavenger), 50 mM taurine (HOCl scavenger), or 2.4 mM L-NAME (NOS inhibitor). In Experiment A, additionally 10 mM mannitol (hydroxyl radical scavenger), 150 µM ABH (peroxidase inhibitor), 100 U/ml MnSOD (superoxide anion scavenger) and 25 µM FeTPPS (peroxynitrite decomposer) were used.

Subsequently, the given concentrations of salicylic acid were added. After 5 hours (A) and 4 hours, respectively, of incubation at 37° C. the percentages of apoptotic cells were determined in duplicate batches according to the classical apoptosis features nuclear condensation, nuclear fragmentation, and membrane blebbing. Here, at least 200 cells were evaluated pre batch.

The result shows that salicylic acid in both cell lines induces ROS-dependent induction of apoptosis that does not depend on singlet oxygen. In the low concentration range of the salicylic acid preferably the NO/peroxynitrite signal path runs, with higher concentrations the HOCl path predominates. The inhibitor profile of the apoptosis induced by salicylic acid in both cell lines is equal to the inhibitor profile that is also shown after the influence of antibodies against catalase. Running of the detected signal chemistry after salicylic acid administration necessarily presupposes that there must have been an inhibition of the protective tumor cell catalase by salicylic acid, since else neither the HOCl nor the NO/peroxynitrite path could have formed.

FIGS. 6 and 7 show the effect of direct catalase inhibitors (namely monoclonal antibodies that are directed against catalase and salicylic acid, respectively) on tumor cells. Said catalase inhibitors lead to the reactivation of the specific intercellular signal paths by reactive oxygen and nitrogen species and subsequently to apoptosis with the overall process being independent of singlet oxygen.

Figure 8:
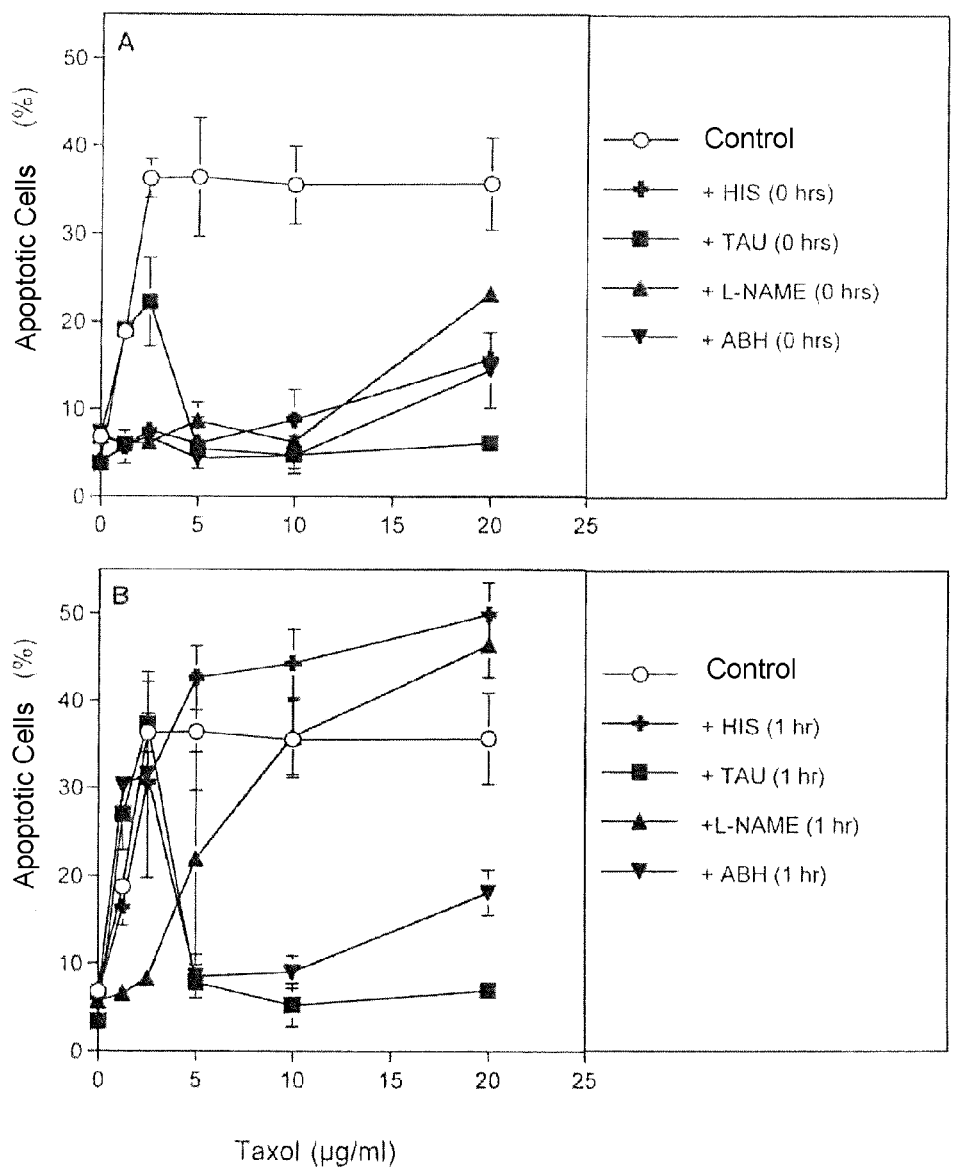

FIG. 8—Induction of apoptosis by taxol is based on singlet oxygen-dependent destruction of the catalase 25 000 Gumbus lymphoma cells in 100 µl medium received the given inhibitors either 10 minutes before taxol addition (A) or 1 hour thereafter (B). Duplicate batches were incubated for 5 hours after taxol addition, before the percentages of apoptotic cells were established. Inhibitors: singlet oxygen scavenger histidine 2 mM; HOCl scavenger taurine 50 mM, NOS inhibitor L-NAME 2.4 mM, peroxidase inhibitor ABH 150 µM.

Induction of apoptosis in Gumbus cells by taxol is caused by a fast singlet oxygen-dependent step that inactivates catalase within the first hour and thus, in the following permits ROS signaling. For the formation of singlet oxygen hydrogen peroxide and peroxynitrite are required. The later signaling at low concentrations of taxol is via the NO/peroxynitrite path, at higher concentrations via the HOCl path.

That is, FIG. 8 shows that taxol (that was characterized as NOD inhibitor) can only induce intercellular signaling and apoptosis if the formation of singlet oxygen is possible, wherein the singlet oxygen-dependent process must proceed very early within the overall happenings to lead to a subsequent effect.

Figure 9:
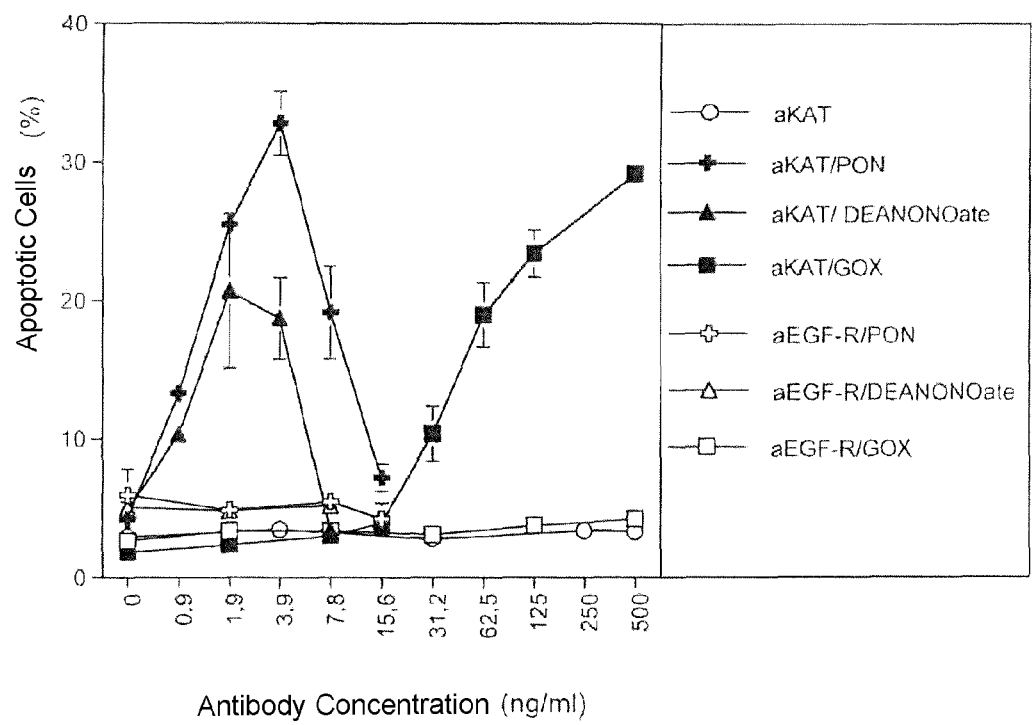

FIG. 9—Direct identification of the catalase inhibition by monoclonal antibodies against catalase 4000 MKN-45 cells per 100 µl in 98 well plates were treated with increasing concentrations of monoclonal antibodies against catalase "Anti-KAT" or Anti-EGFR. After 15 minutes either 200 µM peroxynitrite ("PON"), 0.5 mM DEA-NONOate (rapidly decomposing NO donor), or 2 mU/ml glucose oxidase (GOX) that continuously generates hydrogen peroxide were added. After another two hours at 37° C. the percentages of apoptotic cells were determined in duplicate batches.

The principle of identification is based on the fact that tumor cells (here MKN-45 gastric carcinoma cells) are protected from the apoptosis-triggering effect of exogenously added peroxynitrite by their membranous catalase. Addition of catalase inhibitors sensitizes the cells to the effect of exogenous peroxynitrite. Since with an increasing catalase inhibition hydrogen peroxide is increasingly released it gradually comes to a consumption of peroxynitrite by hydrogen peroxide. This can be seen as an optimum curve of the antibody action. The experiment proves that the monoclonal antibody against catalase by inhibition of their catalase sensitizes the tumor cells to exogenous peroxynitrite as well as peroxynitrite that is formed by the interaction of NO and superoxide anions and hydrogen peroxide.

FIG. 9 represents the identification of the catalase inactivation with tumor cells. It is based on the sensitization of tumor cells to exogenously added peroxynitrite. For specificity control further active ingredients, such as e.g. the NO donor DEA-NONOate and the $H_2O_2$-generateing enzyme glucose oxidase (GOX) were studied. The use of peroxynitrite permits specific measurement of the extracellular, membranous catalase, since intracellular catalase (that is not tumor cell-specific) cannot reach extracellularly added peroxynitrite, before it leads to the lipid peroxidation on the cell membrane.

Figure 10:
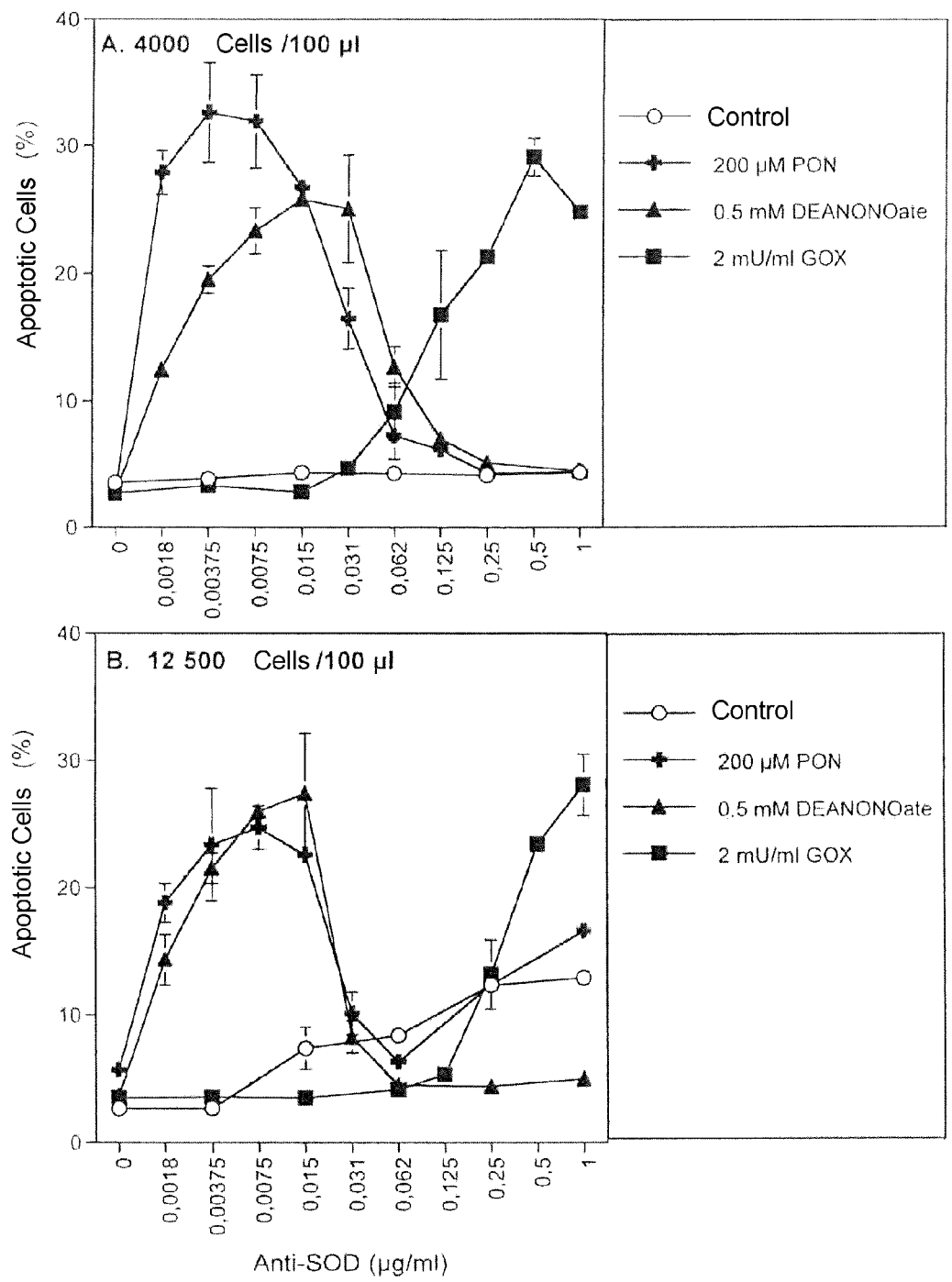

FIG. 10—Anti-SOD leads to sensitization of the cells by catalase inhibition

The experiment was performed in analogy to that described in FIG. 9 except that instead of Anti-KAT a monoclonal antibody against SOD was used. The cells were tested in two different densities, namely 4000 and 12 500 cells per 100 µl. The challenge to test the activity of catalase was carried out with 200 µM peroxynitrite, or 0.5 mM DEA NONOate or 2 mU/ml GOX. The result (after 2 hours incubation time) shows that also Anti-SOD leads to the inhibition of the catalase activity. In parallel performed investigations on the mechanism of this indirect effect show that the superoxide anions present in excess after SOD inhibition lead to an inhibition of the catalase.

FIG. 10 shows that the inhibition of the membranous SOD of the tumor cells inevitably leads to the inhibition of the membranous catalase. Said complementary inhibition is based on the fact that free superoxide anions present in a high concentration after the inhibition of the SOD inhibit the catalase via a 1-electron transfer.

Figure 11:
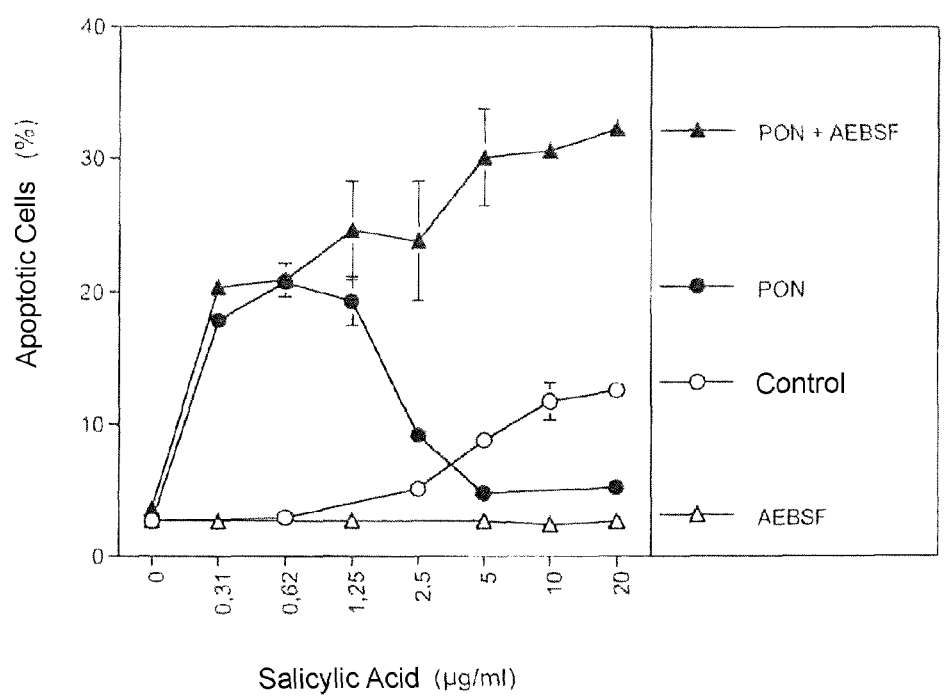

FIG. 11—Salicylic acid inhibits the tumor cell catalase 12 500 MKN cells per 100 µl were pre-treated with the given concentrations of salicylic acid for 15 minutes, in the presence or absence of 100 µM AEBSF, which in turn has been added to the cells 15 minutes before the salicylic acid. Subsequently, 200 µM or no peroxynitrite was added. After 1.5 hours the percentages of apoptotic cells were determined in duplicate batches. The experiment shows that salicylic acid inhibits the catalase of the tumor cells. The inhibition is independent of the superoxide anion synthesis. However, if the superoxide anion synthesis is inhibited there was no consumption of peroxynitrite by hydrogen peroxide and the optimum curve converts to a plateau curve.

Figure 12:
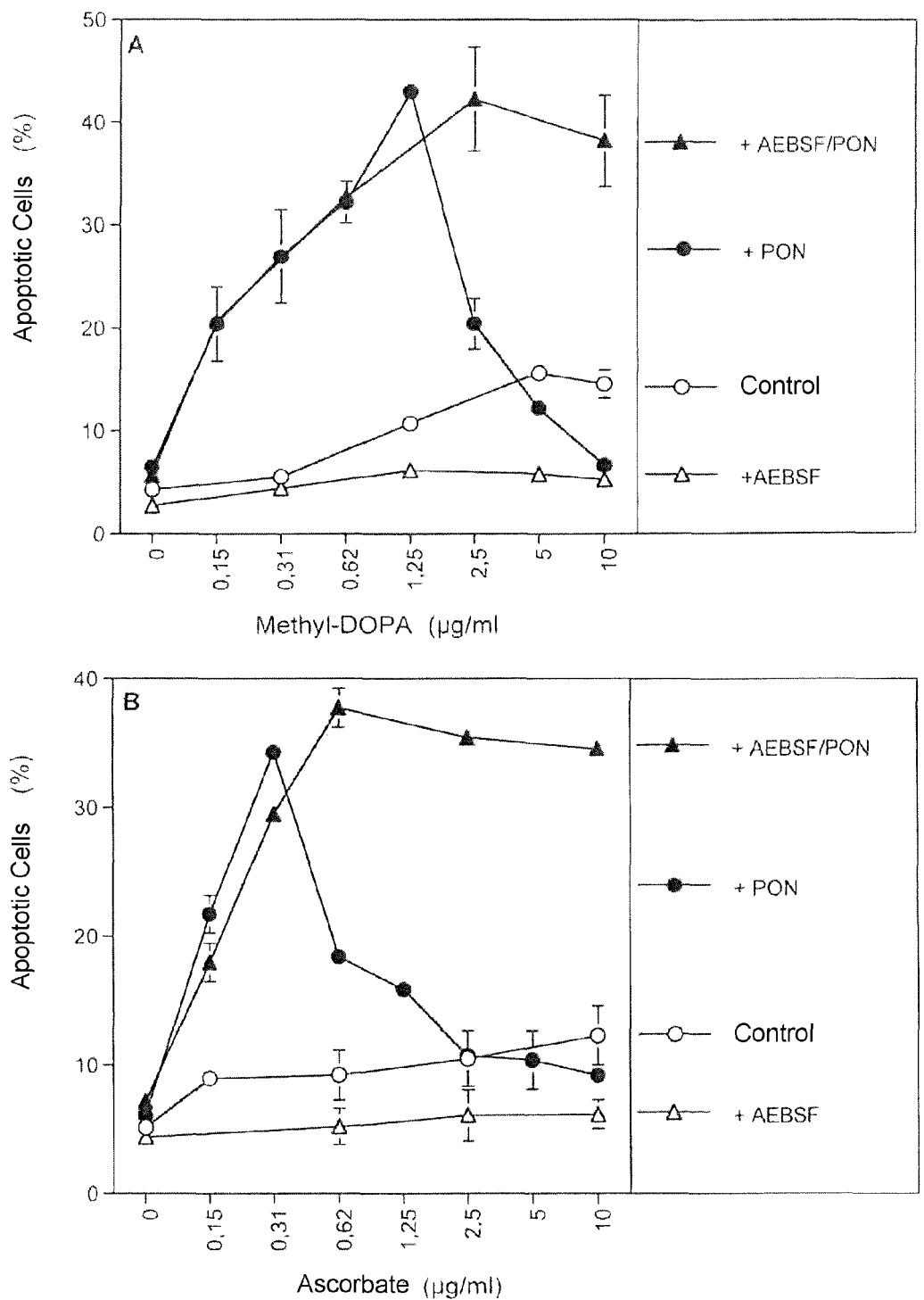

FIG. 12—Inhibition of the tumor cell catalase by methyldopa and ascorbic acid, respectively 12 500 MKN cells per 100 µl were pre-treated with the given concentrations of methyldopa (A) and ascorbic acid (B) for 15 minutes, in the presence or absence of 100 µM AEBSF, which in turn has been added to the cells 15 minutes earlier. Subsequently, 200 µM or no peroxynitrite was added. After 1 hour the percentages of apoptotic cells were determined in duplicate batches.

The experiment shows that both methyldopa and ascorbic acid directly inhibit catalase without the presence of superoxide anions would be necessary for that. This also allows the conclusion that the inhibition of the catalase is independent of singlet oxygen since its formation inevitably presupposes that superoxide anions are available.

FIGS. 11 and 12 show that salicylic acid, methyldopa and ascorbic acid lead to a direct inhibition of the tumor cell catalase. Sensitization of the tumor cells also takes place when no singlet oxygen formation is possible by inhibition of the NADPH oxidase by means of AEBSF.

Figure 13:
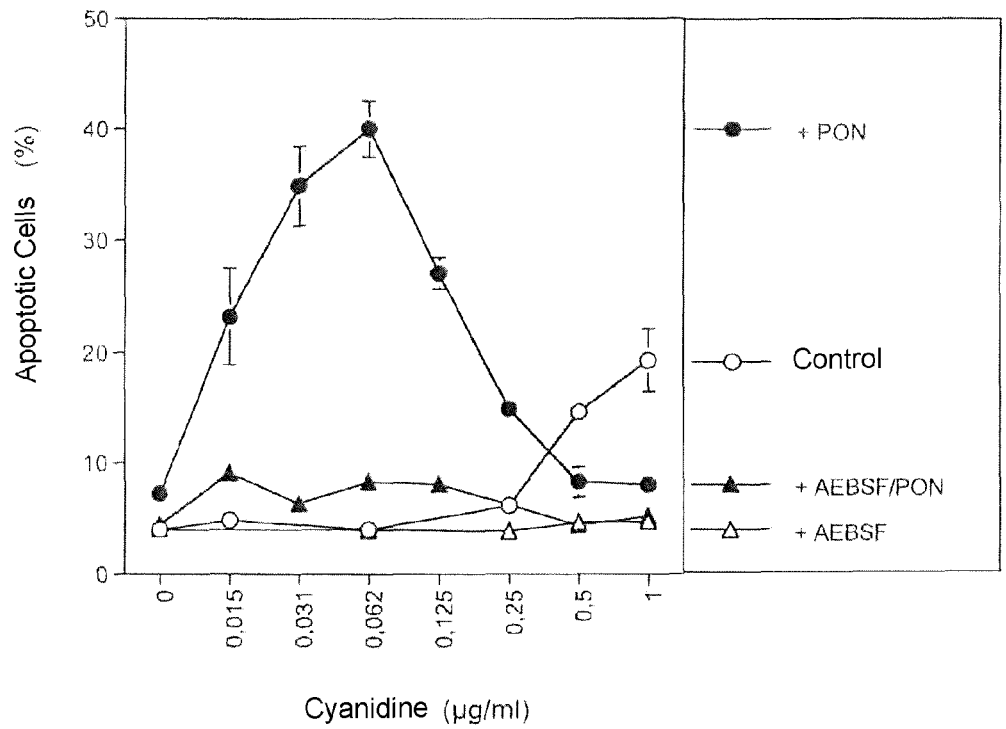

FIG. 13—Inactivation of catalase by cyanidine requires superoxide anions 12 500 MKN-45 cells in 100 µl medium received 100 µM AEBSF or no additive. After 15 minutes the given concentrations of cyanidine were added and the batches were incubated for 15 minutes at 37° C. Subsequently, 200 µM peroxynitrite (PON) were added or the batches were not treated with peroxynitrite (control). After 1 hour the percentages of apoptotic cells were determined in duplicate batches.

The result shows that the inhibiting effect of the cyanidine on the tumor cell catalase depends on superoxide anions. Control investigations show that this is the more complex mechanism of the catalase inactivation after formation of singlet oxygen. Here, superoxide anions are involved as the basis of the formation of hydrogen peroxide and peroxynitrite. The interaction of those two molecules leads to the formation of singlet oxygen. These facts are illustrated in detail in FIG. 20.

FIG. 13 proves that the sensitizing effect of cyanidine (an inhibitor of the NOD) only brings results when superoxide anion synthesis can run. In the presence of the NOX-1 inhibitor AEBSF the tumor cells do not exhibit sensitivity for peroxynitrite.

Figure 14:
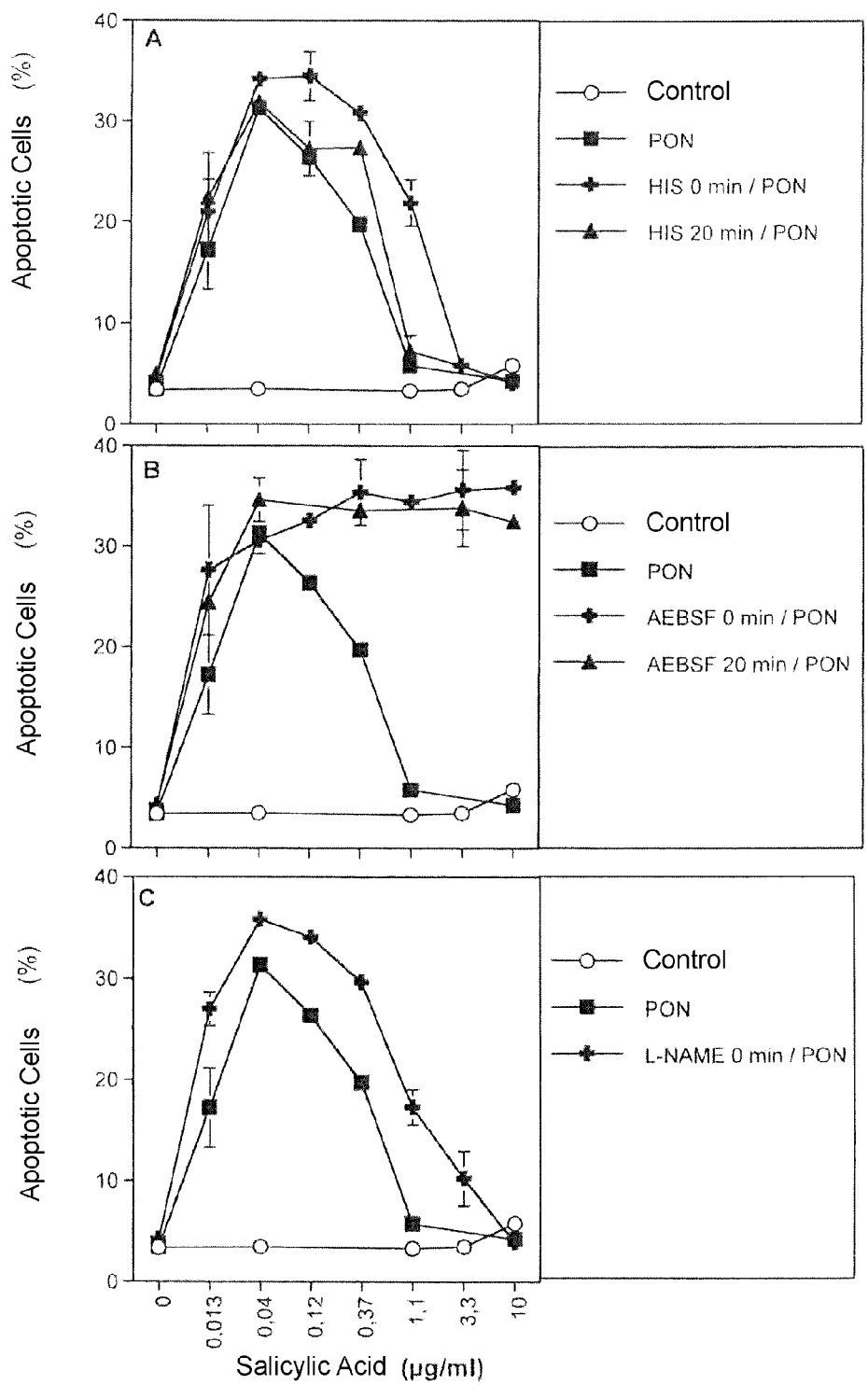

FIG. 14—Catalase inhibition by salicylic acid neither requires singlet oxygen nor superoxide anions nor NO 12 500 MKN-45 cells received no addition (control), or 2 mM histidine, or 100 µM AEBSF or 2.4 mM L-NAME immediately before the addition of the given concentrations of salicylic acid ("0 min") or 20 minutes after addition of salicyl. 20 minutes after the addition of salicylic acid 200 µM peroxynitrite (PON) were added to all batches except the control batches. After another 2 hours the percentages of apoptotic cells were determined in duplicates.

The experiment shows that the addition of the singlet oxygen scavenger histidine or the inhibition of the NADPH oxidase by AEBSF or the inhibition of the NO synthase by L-NAME leads to a reduction of the inhibition of the catalase by salicylic acid. This proves that the inhibition of the catalase by salicylic acid does not require the formation of singlet oxygen.

Figure 15:
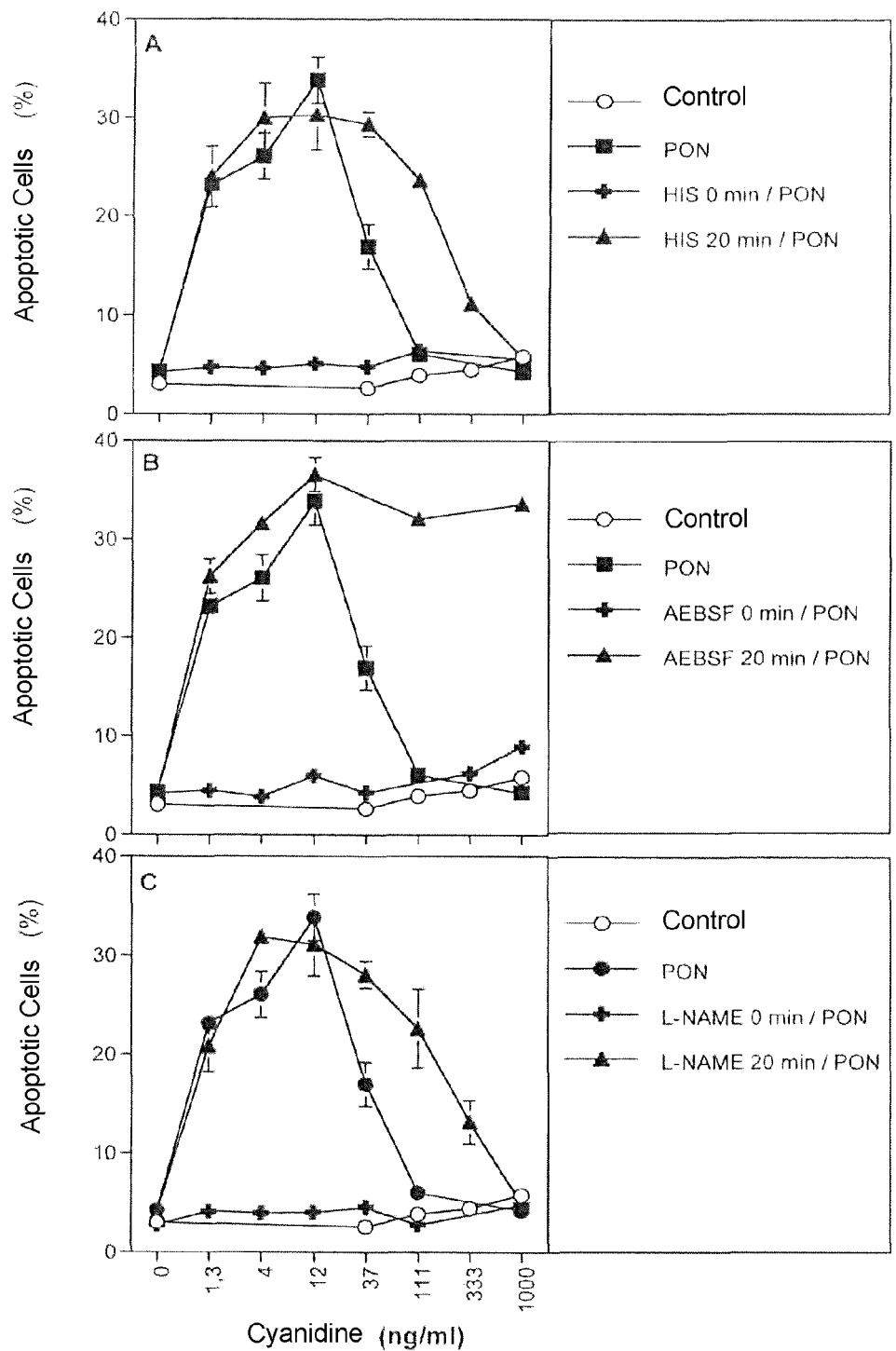

FIG. 15—Inactivation of catalase by cyanidine requires superoxide anions, NO and singlet oxygen 12 500 MKN-45 cells received no addition (control), or 2 mM histidine, or 100 µM AEBSF or 2.4 mM L-NAME immediately before the addition of the given concentrations of cyanidine ("0 min") or 20 minutes after the addition of cyanidine. 20 minutes after the addition of cyanidine 200 µM peroxynitrite (PON) were added to all batches except the control batches. After another 2 hours the percentages of apoptotic cells were determined in duplicate batches.

Unlike salicylic acid (FIG. 14) the inactivation of catalase by cyanidine requires singlet oxygen, superoxide anions and NO. The effect of these three interacting substances takes place early, so that an addition of the inhibitors only at the beginning of the application but not after 20 minutes can prevent inactivation of the catalase.

Due to the established chemistry of the singlet oxygen formation it may be assumed that singlet oxygen is formed by the reaction of peroxynitrite with hydrogen peroxide. Thus, the inhibition of the superoxide anion synthesis both inhibits the peroxynitrite and the hydrogen peroxide development, while the inhibition of the NOS only prevents formation of the peroxynitrite.

Differentiation between direct inhibitors of the catalase and active ingredients that lead to inactivation of the catalase via singlet oxygen formation is illustrated in FIGS. 14 and 15 in greater detail. FIG. 14 shows that the sensitizing effect of salicylic acid is independent of whether superoxide anions can be formed and whether the singlet oxygen scavenger histidine is present in the system. However, cyanidine only leads to a sensitizing effect when superoxide anion synthesis can run immediately before the peroxynitrite challenge and no histidine is present in the system, as shown in FIG. 15.

Figure 16:
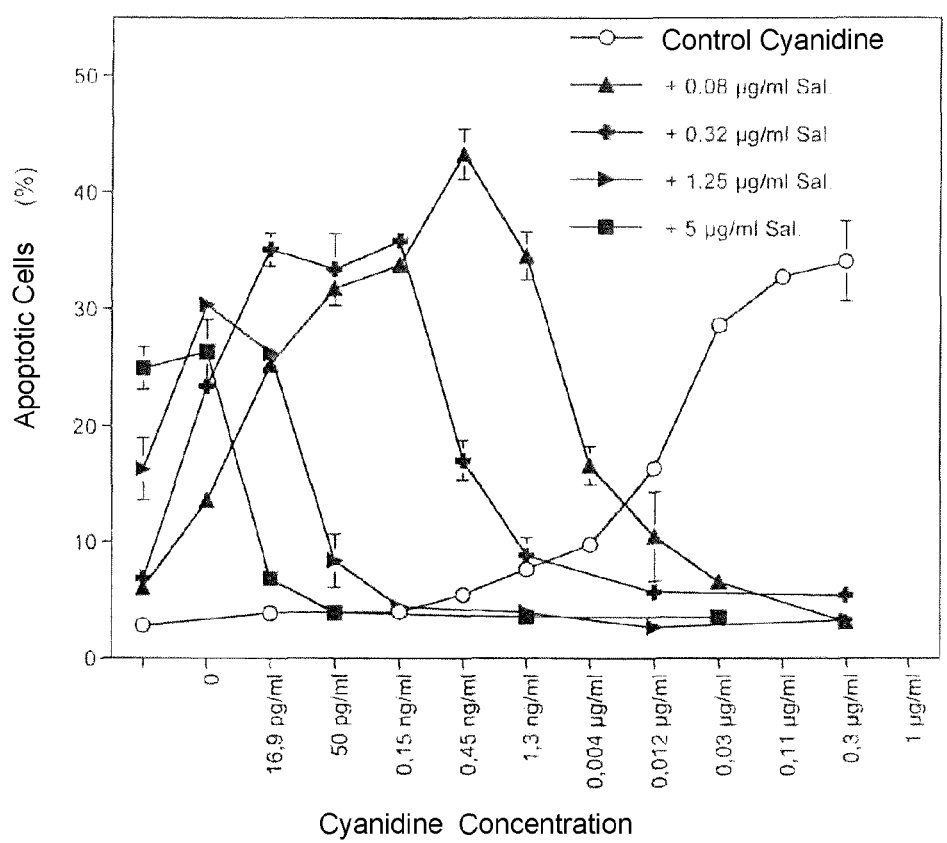

FIG. 16—Synergistic interaction of salicylic acid and cyanidine in the induction of apoptosis of MKN-45 tumor cells 12 500 MKN-45 cells in 100 µl (duplicate batches) were treated with the given concentrations of salicylic acid or remained free from salicylic acid. After 10 minutes the given concentrations of cyanidine were added. The evaluation after 6 hours shows a considerable synergistic effect with the combined addition of the catalase inhibitors salicylic acid and cyanidine which in turn inhibits NOD and via a complex way leads to the singlet oxygen formation and catalase inactivation.

FIG. 16 presents the concentration ratios of the synergistic effect between the direct catalase inhibitor salicylic acid and the singlet oxygen-dependent NOD inhibitor cyanidine.

Figure 17:
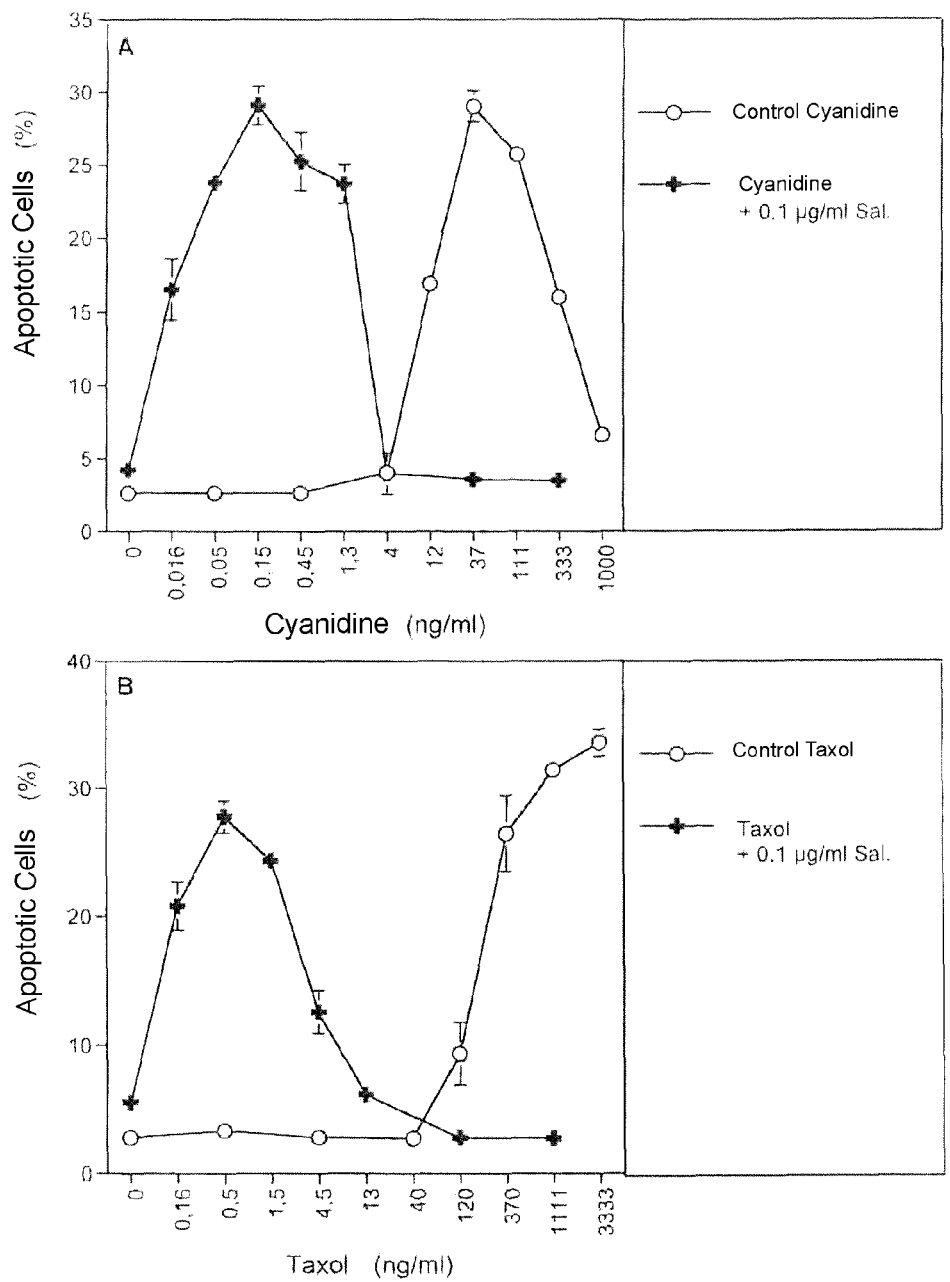

FIG. 17—Synergism between salicylic acid and cyanidine and between salicylic acid and taxol in the induction of apoptosis in tumor cells 12 500 MKN-45 cells in 100 µl (duplicate batches) were treated with 0.1 µg/ml salicylic acid or remained free from salicylic acid (control). After 10 minutes the given concentrations of cyanidine (A) or taxol (B) were added. After 6.5 hours the percentages of apoptotic cells were determined in duplicate batches.

The experiment shows that salicylic acid both with the anthocyane cyanidine and the established chemotherapeutic agent taxol causes a remarkable synergistic effect.

Figure 18:
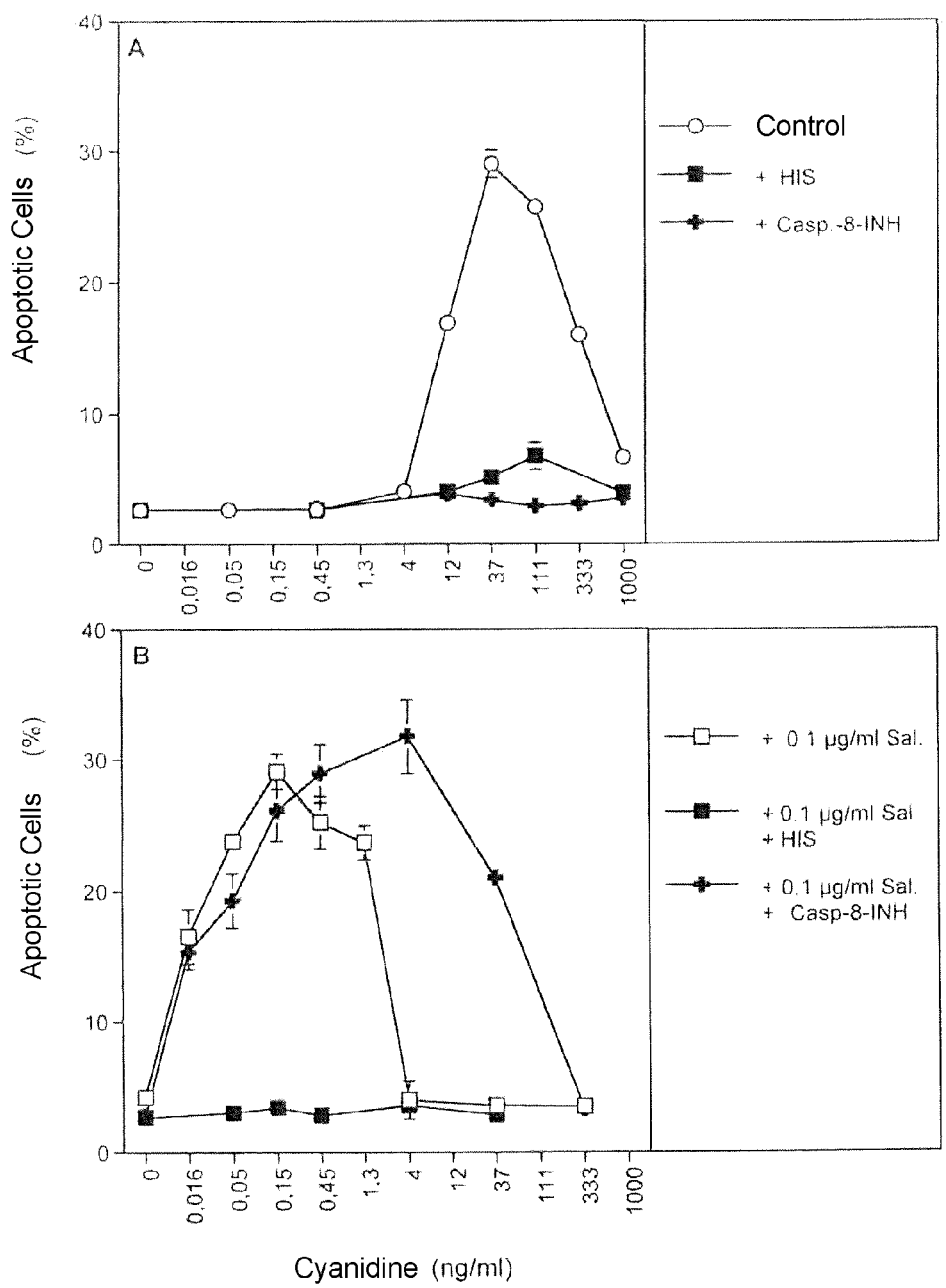

FIG. 18—The synergistic effect between cyanidine and salicylic acid is singlet oxygen-dependent, but independent of Caspase-8

12 500 MKN-45 cells in 100 µl (duplicate batches) either received no additive (control), 2 mM of the singlet oxygen scavenger histidine or 25 µM Caspase-8 inhibitor. After 15 minutes 0.1 µg/ml salicylic acid were added to the batch shown under B, while batch A did not receive further additives. After another 15 minutes cyanidine was added in the given concentrations. After 6.5 hours of incubation at 37° C. the percentages of apoptotic cells were determined.

The experiment shows that the effect of cyanidine both depends on singlet oxygen and the activity of Caspase-8. The distinct synergistic effect between cyanidine and salicylic acid is also based on the effect of singlet oxygen, but is independent of Caspase-8.

Figure 19:
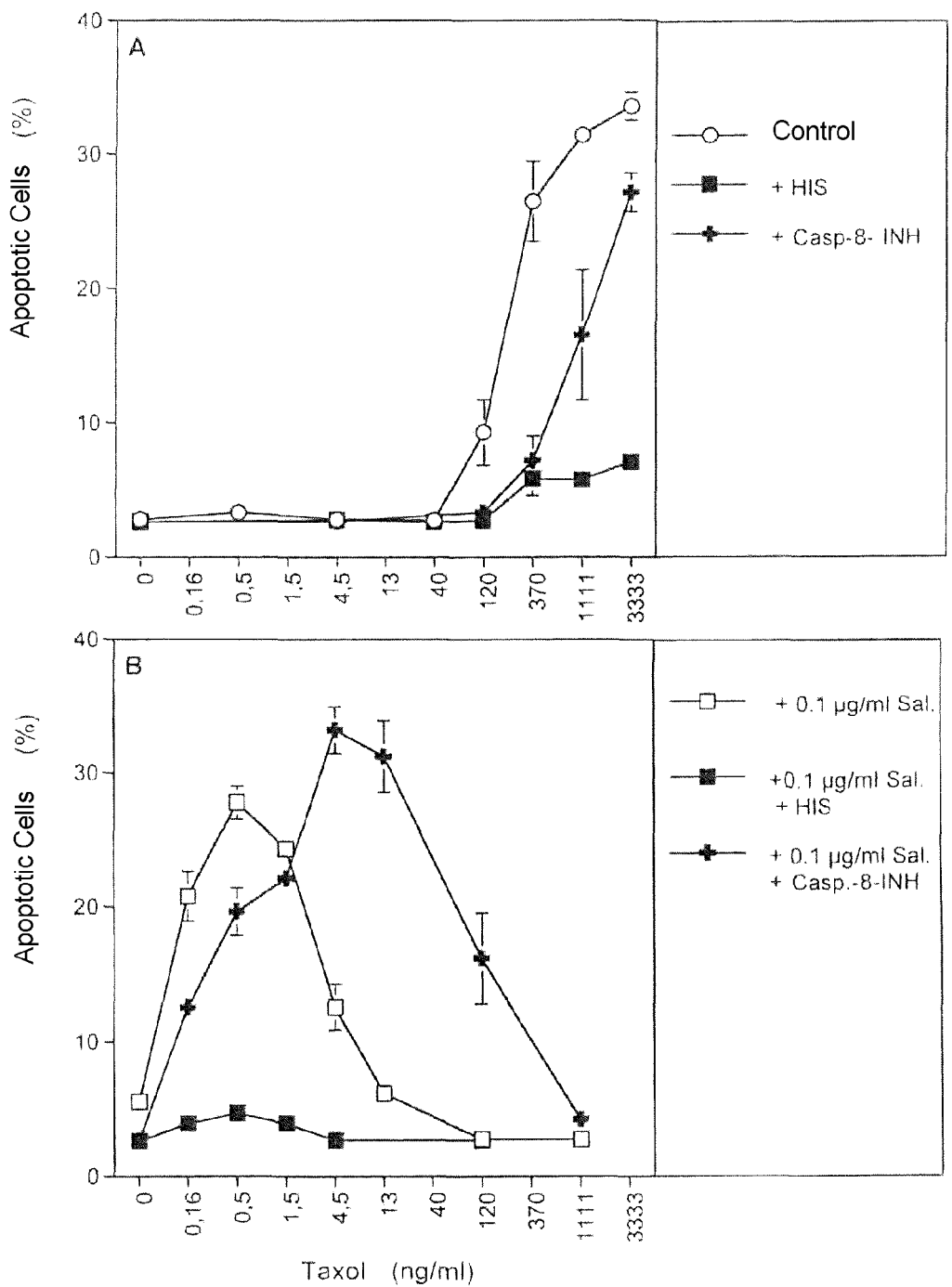

FIG. 19—The synergistic effect between taxol and salicylic acid is singlet oxygen-dependent, and in the high concentration range of taxol independent of Caspase-8

12 500 MKN-45 cells in 100 µl (duplicate batches) either received no additive (control), 2 mM of the singlet oxygen scavenger histidine or 25 µM Caspase-8 inhibitor. After 15 minutes 0.1 µg/ml salicylic acid were added to the batch shown under B, while batch A did not receive further additives. After another 15 minutes taxol was added in the given concentrations. After 6.5 hours incubation at 37° C. the percentage of apoptotic cells was determined.

The experiment shows that the effect of taxol with all concentrations depends on singlet oxygen. However, a necessary involvement of Caspase-8 can only be seen up to 370 ng/ml of taxol, at higher taxol concentrations Caspase-8 is increasingly less required. The synergistic effect between salicylic acid and taxol completely depends on singlet oxygen, but shows only a partial involvement of Caspase-8.

FIGS. 17-19 illustrate in detail the analysis of the synergistic effect between salicylic acid on the one hand and cyanidine or taxol (both NOD inhibitors) on the other hand. Here, also the role of the singlet oxygen and the Caspase-8 in the overall process is examined.

Figure 20:
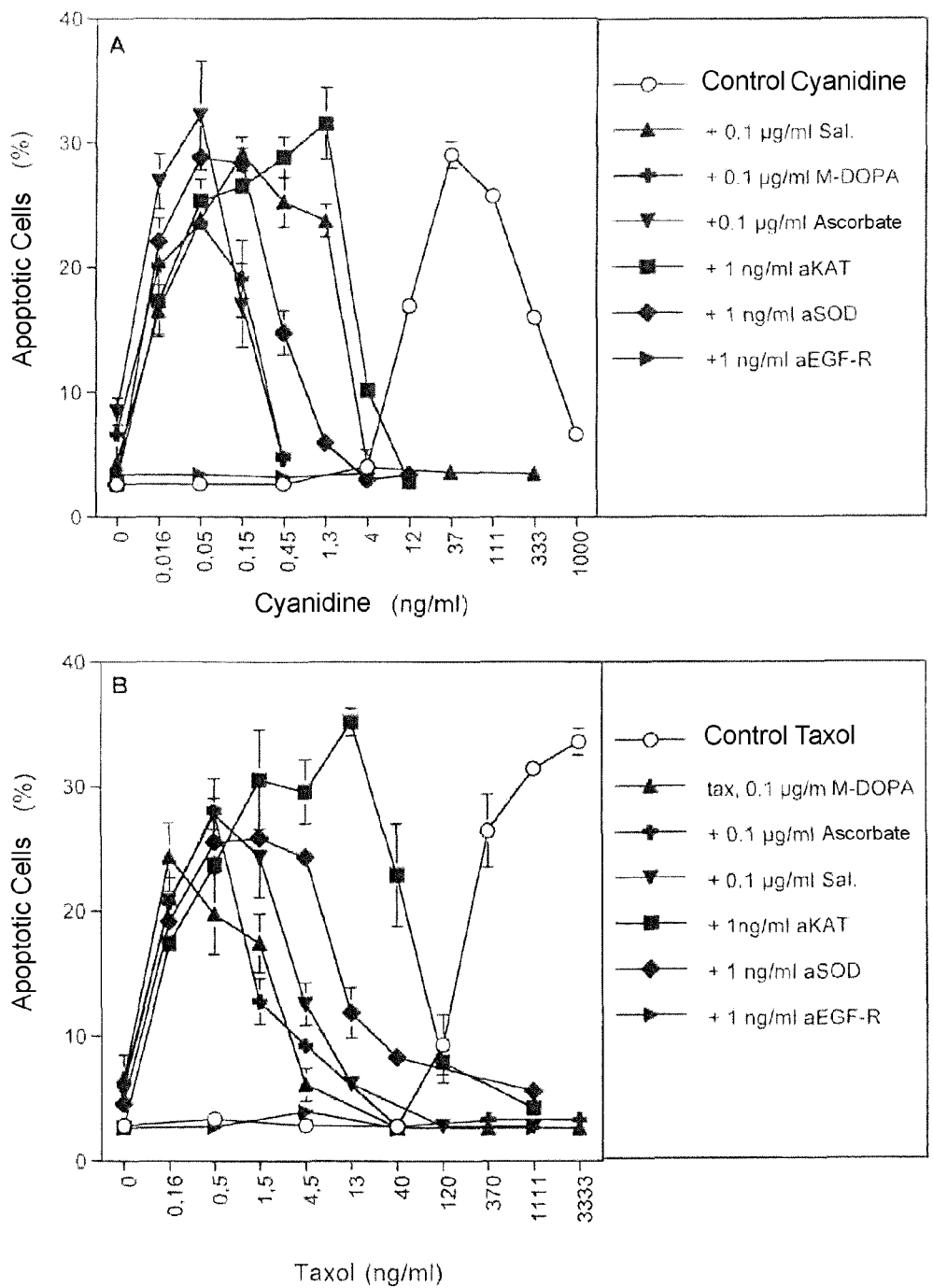

FIG. 20—Synergistic effect of different catalase inhibitors with cyanidine or taxol, respectively 12 500 MKN-45 cells in 100 µl (duplicate batches) received the given concentrations of the direct catalase inhibitors salicylic acid, methyldopa, ascorbate, anti-catalase, anti-SOD and the irrelevant antibody anti-EGF receptor. Control batches remained free from inhibitors. After 15 minutes the given concentrations of cyanidine (A) and taxol (B), respectively, were added. After 6.5 hours of incubation at 37° C. the percentages of apoptotic cells were determined.

This experiment shows that all of the employed direct catalase inhibitors are capable of a synergy effect with cyanidine or taxol.

FIG. 20 shows the broad applicability of the concept of the represented synergy effects. Here, five different direct inhibitors are examined for their synergy effect with cyanidine or taxol.

Figure 21:
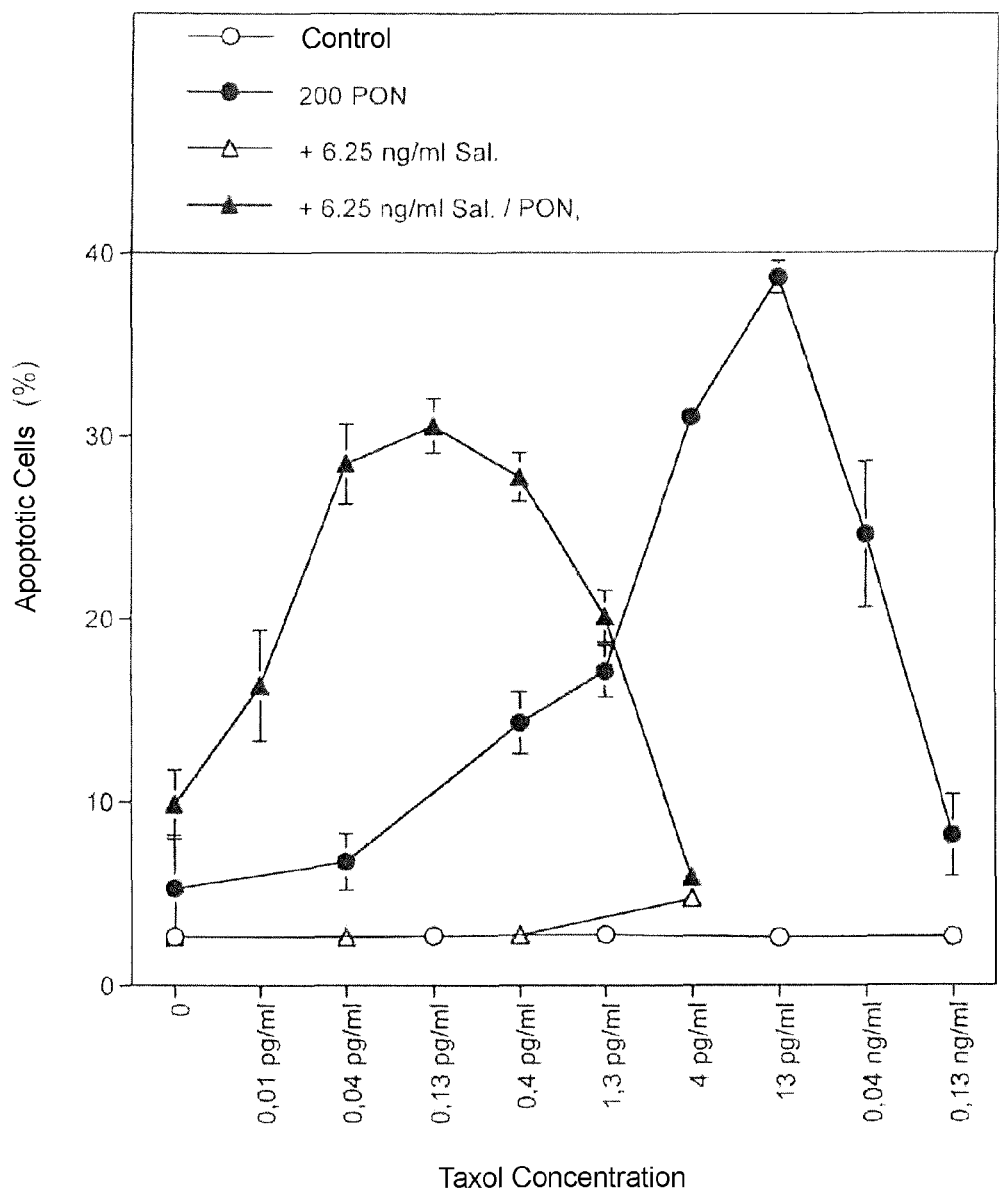
Figure 22:
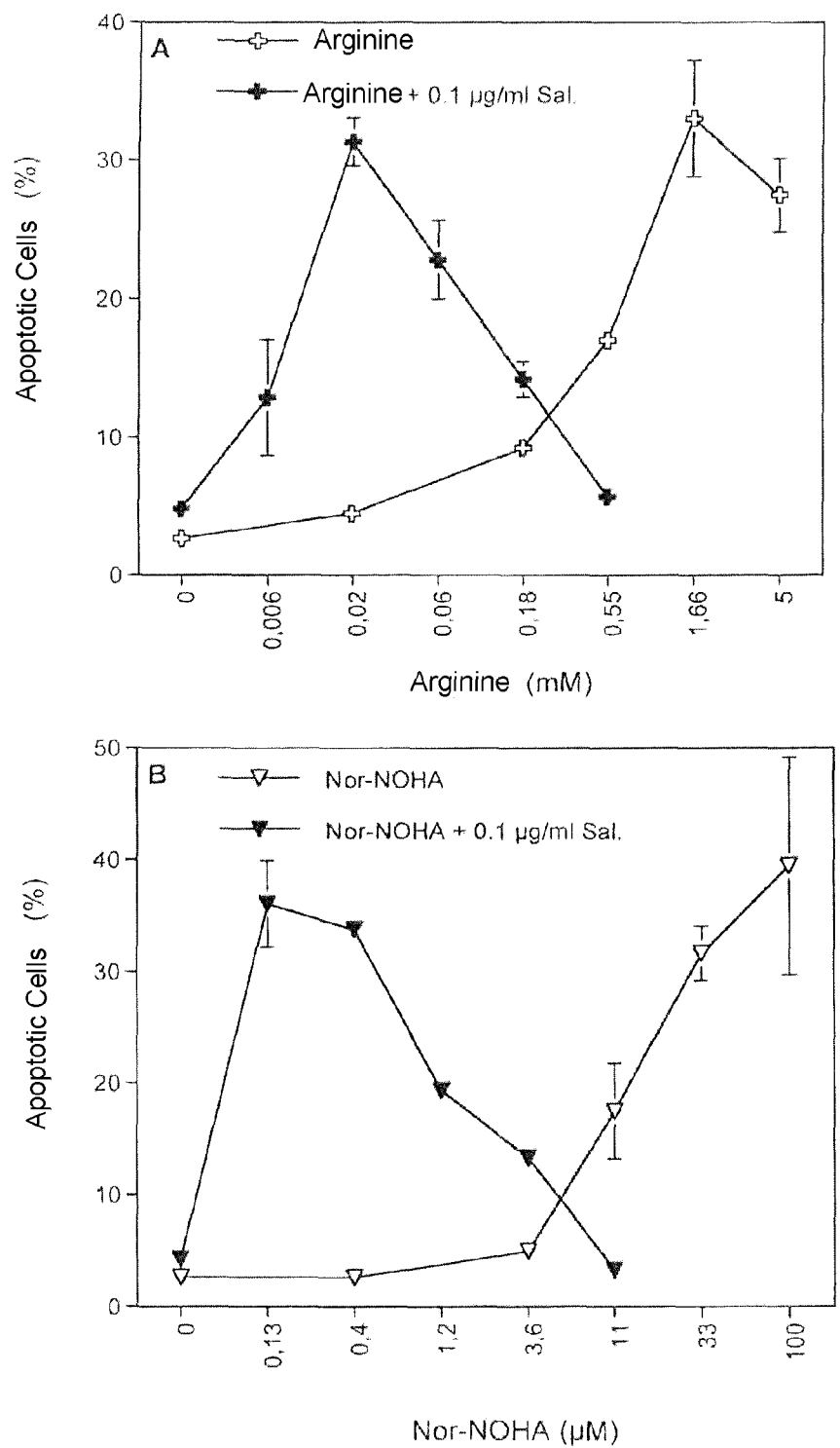

FIG. 21—The synergistic effect between salicylic acid and taxol leads to the catalase inactivation 12 500 MKN-45 cells were treated with the given concentrations of taxol, without and with 6.25 ng/ml salicylic acid for 15 minutes, subsequently 200 µM peroxynitrite were added. After 1.5 hours the percentage of apoptotic cells was measured. There is shown a synergistic effect on the catalase inactivation.

FIG. 21 proves that the synergy effect between salicylic acid and taxol can also be detected when the inactivation of the tumor cell catalase is directly measured.

FIGS. 22-25—The direct catalase inhibitor salicylic acid interacts synergistically with a number of modulators of the NO metabolism or the NOX-1 activity 12 500 MKN-45 cells in 100 µl medium were incubated with increasing concentrations of the given active ingredients, in the presence or absence of 0.1 µg/ml salicylic acid for 6 hours and then, the percentages of the apoptotic cells were determined (repeated determination).

Figure 25:
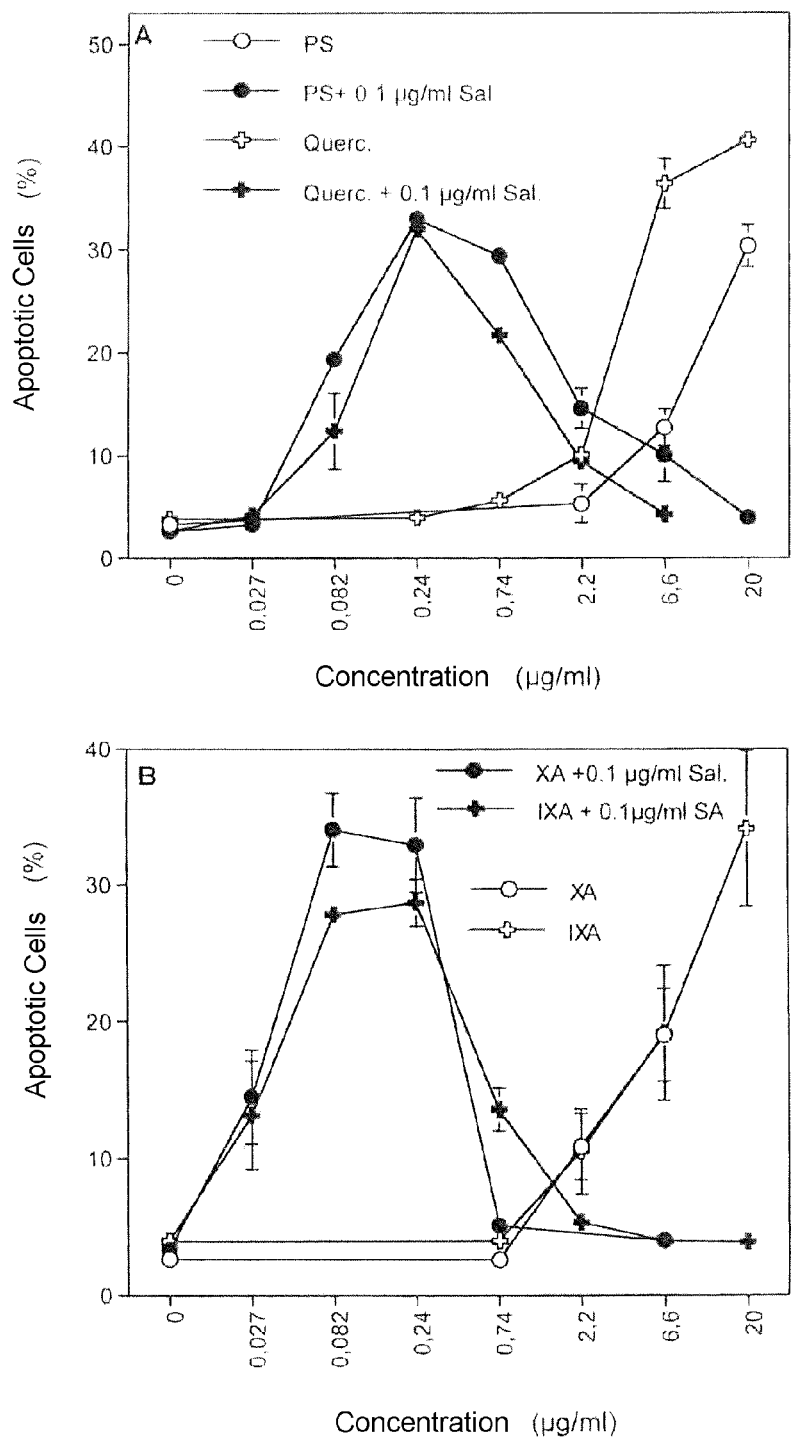

The result shows that salicylic acid synergistically reacts with arginine (FIG. 22, above), the arginase inhibitor NOR-NOHA (FIG. 22, bottom), the stimulator of the superoxide anion production resveratrol (FIG. 23, above), the NOD inhibitors itraconazol, artemisinin (FIG. 23, bottom), diallyldisulfide ("DADS") (but not the inactive diallylsulfide) ("DAS") (FIG. 24, above), allylisothiocyanate ("AITC") (FIG. 24, bottom), palmitic acid (PS) as well as the flavonoids quercetin (FIG. 25, above), xanthohumol (XA), and isoxanthohumol (IXA) (FIG. 25, bottom).

FIGS. 22-25 cite further examples of the broad applicability of the represented new concept. Here, a concentration of salicylic acid, which is ineffective in itself, is combined with a number of modulators of the NO metabolism as well as with the NOX-1 stimulator resveratrol. This, in any case results in a very impressive synergy effect.

Figure 26:
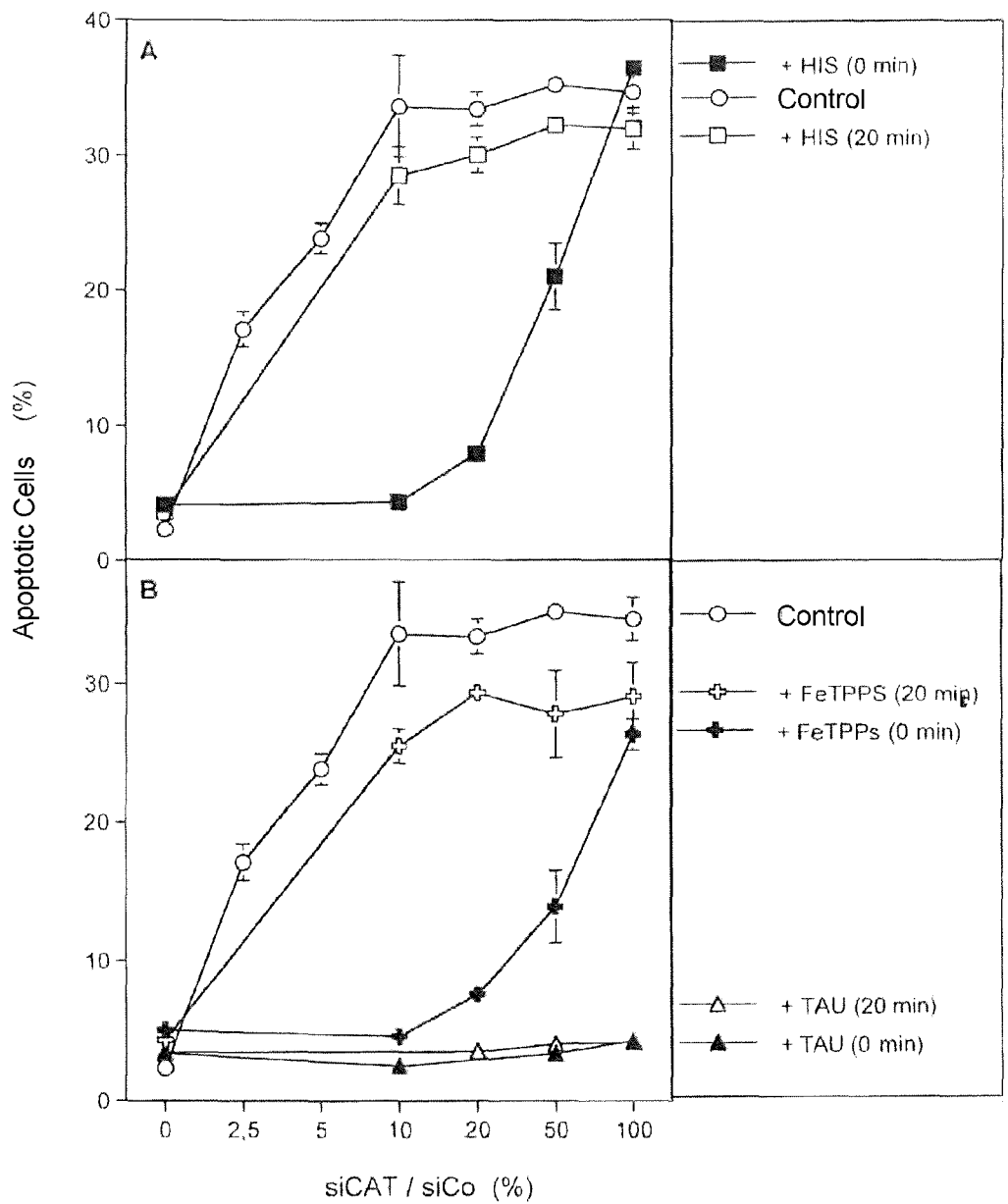

FIG. 26—"Primer function" of the catalase inhibition for the catalase inactivation by singlet oxygen MKN-45 cells were transfected and incubated for 24 hours with 24 nM of a siRNA ("siCAT") directed against human catalase expression or an irrelevant control SiRNA ("siCo"). The details of the transfection and the siRNA used are described in Heinzelmann and Bauer, 2010. After the incubation the cells were washed. SiCo-transfected cells were prepared as pure culture or with an increasing portion of siCAT-transfected cells (12 500 cells/100 µl medium in total). These batches either received no further additives (control) or histidine (2 mM), FeTPPS (25 µM), or taurine (50 mM). The addition of these inhibitors for some of the batches was directly when mixing the differently transfected cells (0) or 20 minutes later. After a total of 4.5 hours the percentages of apoptotic cells were determined in duplicate batches.

The result shows that siCO-transfected cells do not go into apoptosis, while siCAT-transfected cells barely reach 40% of apoptotic cells. If a small percentage of siCAT-transfected cells was mixed to the siCo-transfected cells usually a much higher value for the induction of apoptosis is achieved than would have been expected from the mixing ratio.

If the singlet oxygen scavenger histidine or the peroxynitrite scavenger FeTPPS are already added when mixing the two cell populations this results in a degree of the induction of apoptosis that corresponds to the portion of the admixed siCAT cells. If the two inhibitors are added 20 minutes later this nearly results in the picture of the non-inhibited control batch.

This result thus shows that starting from a few cells with lacking catalase a quasi-infectiously spreading inactivation of the catalase of the adjacent cells is achieved. In this "bystander effect" peroxynitrite and the resulting singlet oxygen play an essential role.

Figure 27:
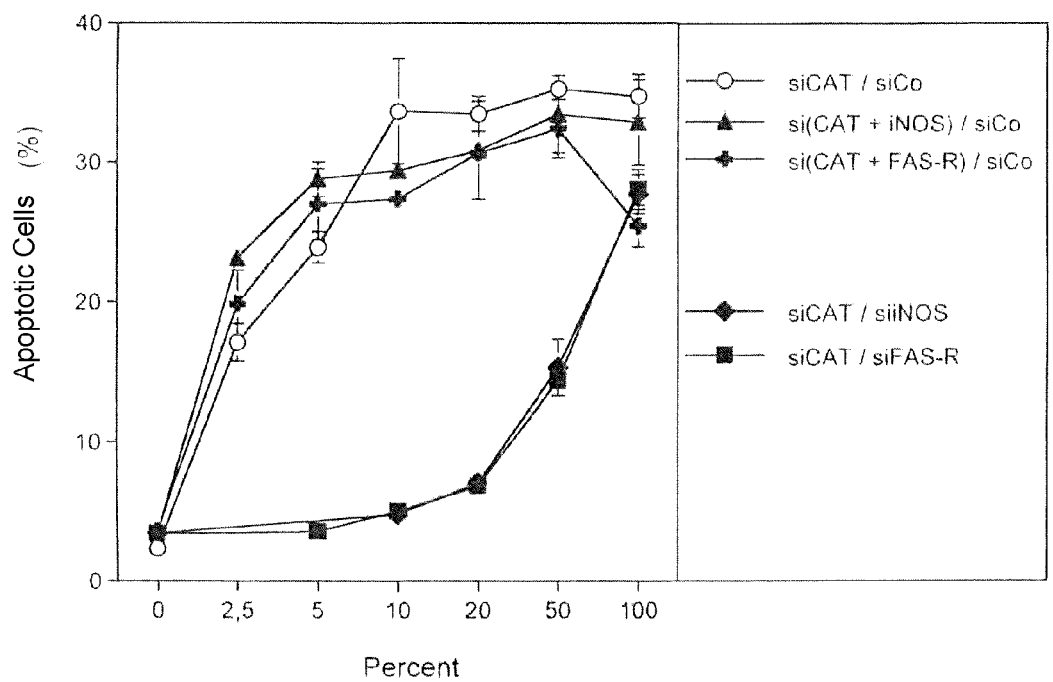

FIG. 27—Requirements for the intercellular spreading of the catalase inactivation MKN-45 cells were transfected with the following siRNA (combinations):

Control-siRNA (siCo), siRNA against catalase (siCAT), siRNA against iNOS (siiNOS), siRNA against the FAS receptor (siFAS-R), a mixture of siCAT plus siiNOS [si(CAT+iNOS)] and a mixture of siCAT and siFAS-R [si(CAT+FAS-R)].

After 24 hours the given mixtures were prepared from the given groups (12 500 cells per 100 µl medium), incubated and after 4.5 hours the percentages of apoptotic cells were determined.

The experiment shows that the inactivation of the catalase of the adjacent cells starting from the siCAT-transfected cells can also run when the siCAT-transfected cells have no iNOS or FAS receptor.

On the other hand, the reactivity of the cells with previously intact catalase depends on that they have iNOS and FAS receptor. This, in total indicates a complex process that runs in several stages, wherein starting from a few cells with lacking catalase in adjacent cells catalase inactivation takes place with the participation of the FAS system and NO.

Figure 28:
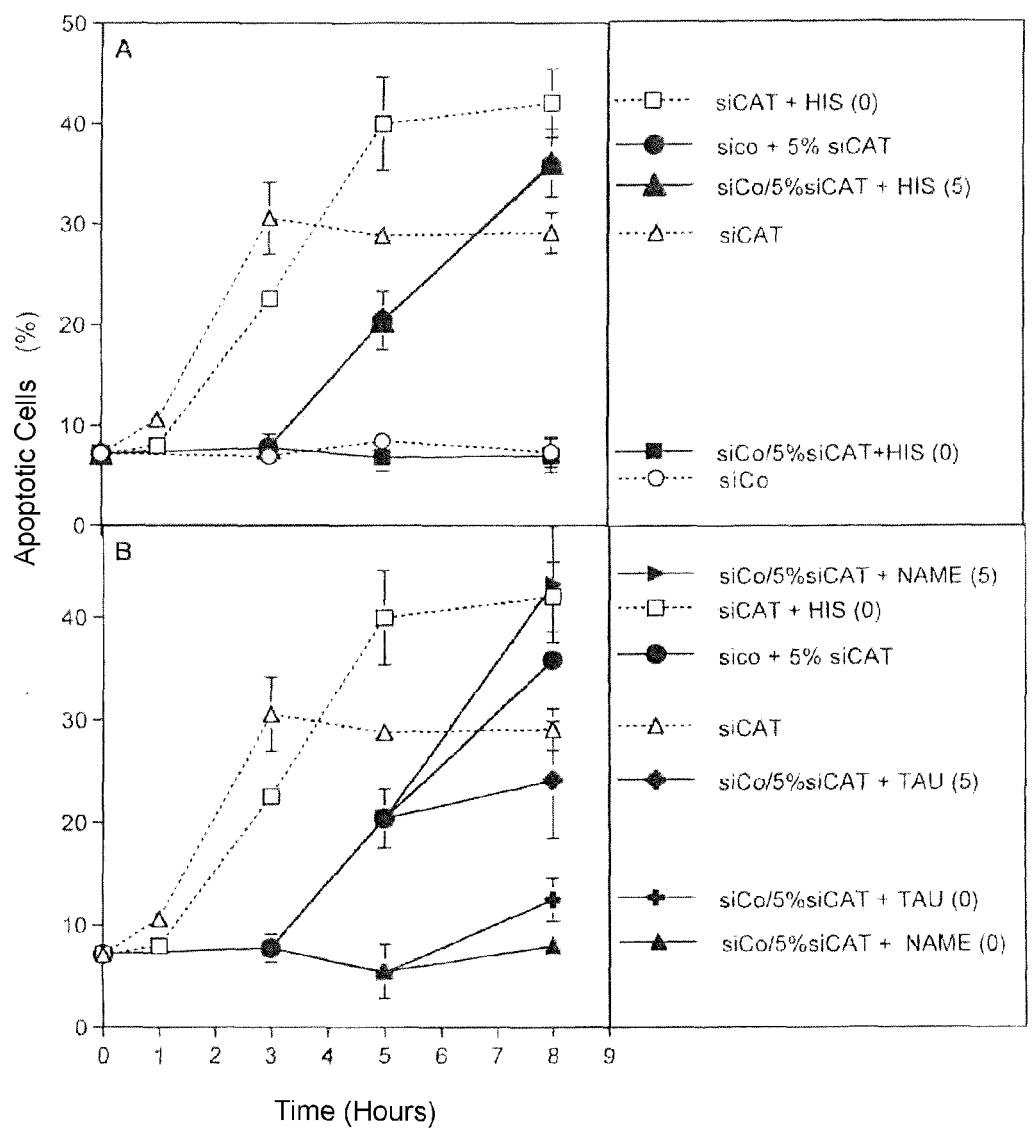

FIG. 28—Kinetic analysis of the intercellular spreading of the catalase inactivation MKN-45 cells were transfected with siCO or siCAT (24 nM) and incubated for 24 hours. Then, pure cultures of the two cell populations or a mixture of 5% siCAT-transfected with 95% siCo-transfected cells were prepared. In all batches a cell density of 12 500 cells per 100 µl was set.

The batches either remained free from inhibitors or received 2 mM histidine, 2.4 mM L-NAME or 50 mM taurine from the beginning (0) or after five hours (5). The percentages of apoptotic cells were determined at the given times.

The result shows that siCAT-transfected cells go very fast into apoptosis wherein then the reaction already arrests after 2 hours. In the presence of histidine the slope of the apoptosis curve is slightly delayed, but the arrest is later and on a higher apoptotic level. That is, histidine slightly slows down the apoptotic kinetics, but at first also prevents the reaction from running out of the optimum. SiCo-transfected cells exhibit no induction of apoptosis during the period of observation. If 5% siCAT-transfected cells were admixed to the siCo-transfected cells this after a three-hour period of latency results in a sharp slope of the apoptotic kinetics. This slope is completely prevented when histidine was present in the system from time 0. However, addition of histidine at 5 hours time has no effect on the induction of apoptosis. The same pattern is obtained for the effect of the NOS inhibitor L-NAME. Addition of taurine at 0 hours time results in a barely complete inhibition of the apoptosis, however, unlike the other two inhibitors, addition at 5 hours time achieves an immediate arrest of the induction of apoptosis. This complex happenings can be explained as follows: Within the latency stage starting from the siCAT cells an inactivation of the catalase in siCo cells takes place, wherein singlet oxygen and NO play a central role. The inactivation of the catalase in the whole population of the cells now permits running of the HOCl path that can be interrupted at any time by taurine.

Figure 29:
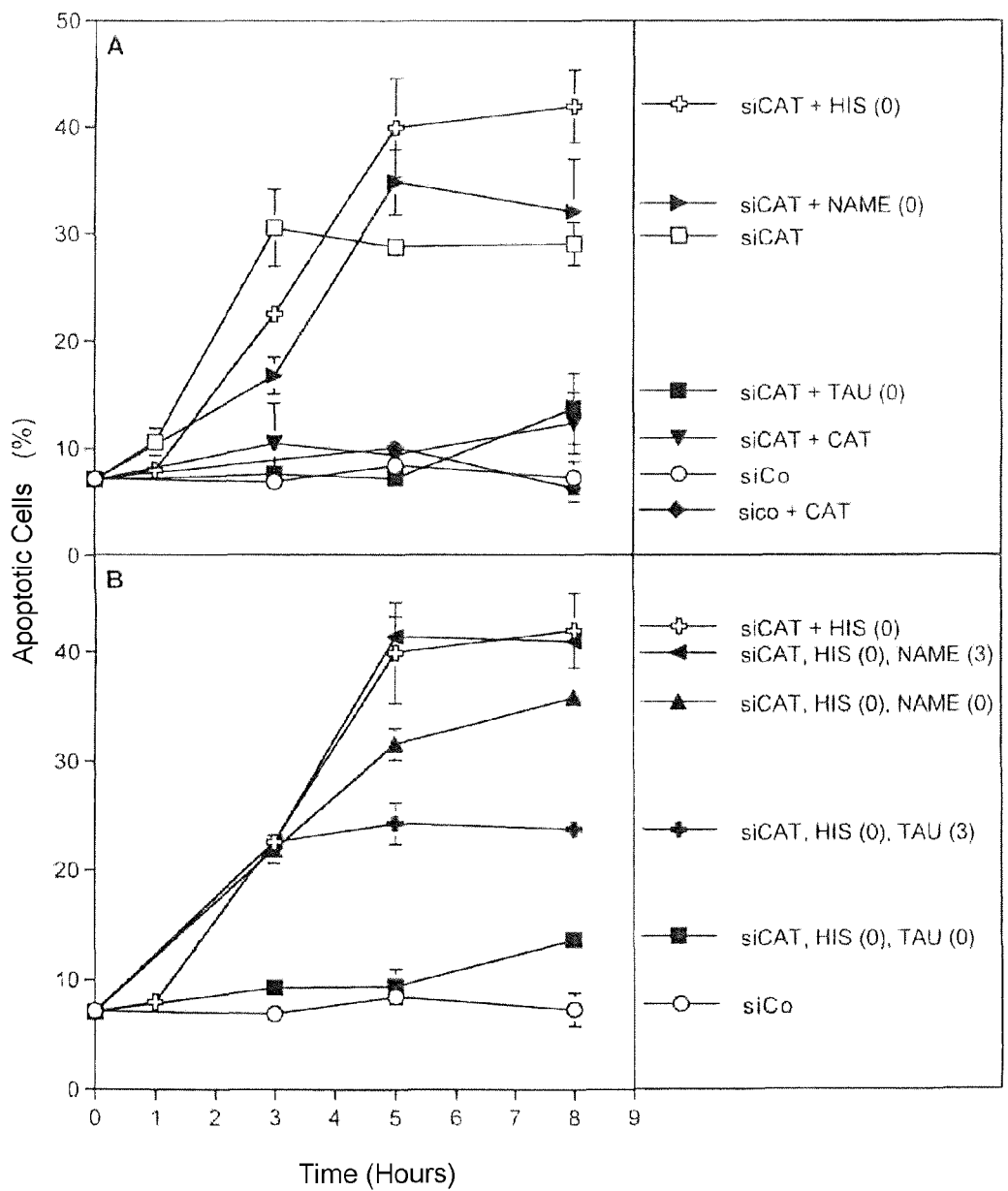

FIG. 29—Control studies on the experiment shown in FIG. 28

The experimental design corresponds to the experiment described in FIG. 28. The same cell populations (siCo and siCAT) were used.

The data show that supplementation of the siCAT cell population with exogenous catalase ("CAT", 30 U/ml) again cancels the effect of the siRNA-dependent catalase knock-down and thus, proves its specificity. With the induction of apoptosis in siCAT-transfected cells, with or without the addition of histidine, this is mainly the HOCl path (inhibitability by taurine) and only to a small extent a participation of NO.

FIGS. 26-29 represent model experiments that show the "quasi-infectious" spreading of the catalase inactivation starting from tumor cells with lacking catalase (siRNA knockdown) within the cell population with originally intact, protective catalase. Said process is mediated by singlet oxygen and essential for the understanding of the at first unexpected synergistic effect between direct catalase inhibitors and the active ingredients modulating by NO or superoxide anions and destroying catalase by means of singlet oxygen formation.

EXAMPLES

Example 1

1.1 Characterization of the Various Effects on Catalase

FIG. 6 summarizes the main characteristics of the induction of apoptosis in the gastric carcinoma cell line MKN-45 after administration of an active ingredient that directly inhibits catalase, namely the monoclonal antibody against catalase. There is apoptosis depending on the antibody concentration until an optimum, subsequently there results a supra-optimal decline of the curve. The induction of apoptosis after antibody-mediated catalase inhibition is independent of singlet oxygen, since no inhibition by histidine can be observed. The induction of apoptosis depends on extracellular superoxide anions over the entire concentration range of the antibody, since it is completely blocked by AEBSF, an NADPH oxidase inhibitor, and by SOD. The intracellular courses of the apoptosis are mediated by Caspase-9 and Caspase-3 what permits conclusion on the mitochondrial path of the apoptosis. As expected, death receptors are not involved in the induction of apoptosis, since the Caspase-8 inhibitor exhibits no inhibiting effect. FIG. 6B proves that in the low concentration range of the antibody preferably the NO/peroxynitrite path runs, since there is an inhibition of the apoptosis if the NO synthase is blocked by L-NAME or the developing peroxynitrite is destroyed by FeTPPS (a catalytically acting peroxynitrite decomposer "peroxynitrite decomposition catalyst"). With an increasing antibody concentration the NO/peroxynitrite path is replaced by the HOCl path, as can be seen from the inhibitability by ABH, a peroxidase inhibitor and by taurine, a HOCl scavenger. The inhibitability by the hydroxyl radical scavenger mannitol in the entire concentration range of the antibody is explained by the fact that hydroxyl radicals in both signaling paths represent the actual apoptosis-triggering radical. In the NO/peroxynitrite path these are developed by hemolytic decomposition of the peroxynitrite acid, in the HOCl path after interaction between HOCl and superoxide anions.

FIG. 7 demonstrates that salicylic acid in the gastric carcinoma cell line MKN-45 and in the lymphoma cell line Gumbus triggers apoptosis in the same manner and due to the same signaling paths as demonstrated in the preceding FIG. 6 for antibodies directed against catalase and recently also published for the catalase inhibitor 3-aminotriazole (Heinzelmann and Bau-Bauer, 2010). Also here, the lacking inhibitability by histidine is an indication to the direct inhibition of the catalase by salicylic acid, independent of a singlet oxygen action. Salicylic acid was characterized as inhibitor for the catalase of human tumor cells by screening by means of the method described in DE 103 58 077 A1 2005.07.28. With the same test system also ascorbic acid and M-Dopa were identified as direct catalase inhibitors.

The indirect inactivation of the catalase caused by modulation of the NO metabolism and subsequent singlet oxygen formation is contrary to the direct inhibition of the tumor cell catalase. It is exemplary illustrated in FIG. 8 for taxol. Analogue data are present for a series of further natural substances, including flavonoids, anthocyanes, diallyldisulfide, artemisinin, palmitic acid, isothiocyanates such as e.g. methylisothiocyanate, allylisothiocyanate, and sulforaphan, as well as various azoles such as e.g. itraconazole, econazole, fluconazole, miconazole, ketoconazole. FIG. 8 shows that the apoptosis-triggering effect of taxol is inhibited when upon addition of taxol singlet oxygen is caught by histidine or the NO synthase is blocked. One hour later the inhibition profile changes and the reaction again is divided into the NO/peroxynitrite path and subsequently the HOCl path. Further model studies in total lead to the picture that in a first step singlet oxygen is formed that inactivates the catalase, which then enables the classical signaling via the known signaling paths. In this system NO and the peroxynitrite formed thereof have a dual function. At the beginning of the taxol treatment NO and peroxynitrite are required as components for the singlet oxygen formation within the entire concentration range of the taxol. After the extremely rapid inactivation of the tumor cell catalase then NO and peroxynitrite are required for the actual intercellular apoptosis signaling only in the low concentration range of the taxol, while with higher concentrations of taxol the HOCl path becomes effective.

In the experiments illustrated in FIGS. 9-15 the effect of various groups of substances on the catalase is directly studied. For that, tumor cells are treated with an increasing concentration of the substance to be tested and subsequently provided with an excess of exogenous peroxynitrite. With an intact catalase there is no induction of apoptosis in the tumor cells, however in case of inhibited or inactivated catalase there is a very rapid induction of apoptosis by the peroxynitrite that is no longer destroyed. Due to the fast reaction after administration of exogenous peroxynitrite in this procedure the autocrine induction of apoptosis of the cells is largely left out of account and there is a valuable focusing on the catalase effect.

FIG. 9 shows that antibodies against catalase, but not an irrelevant antibody (here, against the EGF receptor) sensitize cells to the peroxynitrite effect. The reaction shows the picture of an optimum curve that can be explained by the negative effect of excessive hydrogen peroxide on peroxynitrite (Heinzelmann and Bauer, 2010). The same picture emerges when an NO donor (DEA-NONOate) is applied instead of exogenous peroxynitrite. The NO very rapidly released by it reacts with the extracellular superoxide anions generated by NOX-1 to peroxynitrite. At higher antibody concentrations the cells are finally sensitized to the direct induction of apoptosis by an exogenous hydrogen peroxide generator (glucose oxidase). That is, these findings confirm the catalase-inhibiting effect of the monoclonal antibody against catalase.

FIG. 10 shows that antibodies against SOD can trigger the same effect on the catalase as shown above in FIG. 9 for anti-CAT. This unexpected finding is explained by the fact that the membranous catalase of the tumor cells is supported by a membranous SOD in the inhibition of the intercellular signaling paths (EPA 11170076.1). However, after inhibition of the SOD superoxide anions that are now locally present in a very high concentration lead to an inhibition of the adjacent catalase. Now, this leads to the actual sensitization of the cells for the action of peroxynitrite.

FIG. 11 proves that salicylic acid also leads to an inhibition of the catalase that manifests in a sensitization to exogenous peroxynitrite. With a simultaneous inhibition of the NADPH oxidase by AEBSF the consumption reaction between peroxynitrite and hydrogen peroxide is canceled and the optimum curve is converted to a plateau curve. The same facts, that is direct catalase inhibition, applies for methyldopa and ascorbic acid, as is demonstrated in FIG. 12.

Also, the action of the anthocyan cyanidine chloride leads to a sensitization to peroxynitrite, as shown in FIG. 13. However, in inhibition of the superoxide anion production by AEBSF sensitization by cyanidine remains unsuccessful. That is, here a clear separation from the mode of action of the previously discussed group (salicylic acid, methyldopa, ascorbic acid) is possible. This is explained by the fact that here no direct catalase inhibition is achieved, but a more complex, ROS-dependent catalase inactivation step. This is the singlet oxygen-dependent inactivation step that is initiated by a number of modulators of the NO metabolism.

The biochemical difference between direct catalase inhibition (independent of ROS interactions and singlet oxygen formation) and indirect sensitization based on catalase destruction with the participation of ROS interactions and singlet oxygen is represented in FIGS. 14 and 15. While the inhibition effect of salicylic acid on tumor cell catalase is independent of superoxide anions, NO and singlet oxygen (FIG. 14) a strong dependence of the cyanidine effect of superoxide anions, NO and singlet oxygen is shown (FIG. 15).

1.2 Synergistic Effect of Catalase Inhibitors and Modulators of the NO Metabolism or the Production of Extracellular Superoxide Anions The synergistic effect between a direct catalase inhibitor (here, exemplary salicylic acid) and an NO modulator leading to a singlet oxygen-dependent catalase destruction (here, exemplary cyanidine) is systematically examined in FIG. 16. Cyanidine, applied alone, leads to a concentration-dependent induction of apoptosis that reaches its half-maximum value at about 0.02 μg/ml and its optimum at 0.3 μg/ml. When administered alone, salicylic acid shows almost no effect up to 0.32 μg/ml and then, an increasing effect at higher concentrations. The combination of these two substances leads to a very marked synergistic effect. Thus, e.g. the combination of 0.15 ng/ml cyanidine with 0.08 μg/ml salicylic acid enables the maximum induction of apoptosis, while the use of the two substances alone and at the same concentration remained ineffective.

The repeatability and impressive strength of this synergism is demonstrated in FIG. 17 for the interaction between a low and thus, a concentration of salicylic acid, which is ineffective in itself, on the one hand and cyanidine or taxol on the other hand.

FIG. 18 proves that the effect of cyanidine alone both depends on the activity of dead receptors (such as FAS) and the thus activated Caspase-8 and on the development of singlet oxygen. Certainly, the synergistic effect between salicylic acid and cyanidine is also a singlet oxygen-dependent process, what is proven by the inhibitability by histidine, but now no Caspase-8-dependent enhancement of the signaling paths is required.

This experiment shows that the concentration of 0.1 μg/ml of salicylic acid, which is ineffective in itself, makes the singlet oxygen-dependent process controlled by cyanidine much more effective and thus, shifts the concentration dependence for cyanidine far to the left. Moreover, the Caspase-8-dependent amplification step can be omitted if cyanidine and salicylic acid cooperate synergistically.

The picture becomes even more differentiated if the interaction of taxol with salicylic acid and the taxol's effect alone are examined (FIG. 19). The taxol's effect alone is based on singlet oxygen and the effect of Caspase-8 in the low concentration range, but not at higher concentrations. With the synergistic effect the same picture emerges as shown before for the interaction of salicylic acid and cyanidine. These data show that the amplification effect by Caspase-8 that is required under certain conditions becomes dispensable if a sub-toxic concentration of a catalase inhibitor interacts with a modulator of the NO concentration.

The very wide applicability and universality of the presently described new method is illustrated in FIG. 20. Here, both cyanidine and taxol exhibit a considerable synergistic effect if they are combined with sub-toxic concentrations of several active ingredients for which a direct inhibiting effect on catalase has been demonstrated above. Synergism is achieved by the administration of sub-toxic concentrations of salicylic acid, methyl-DOPA, ascorbic acid, anti-CAT, anti-SOD, but not anti-EGFR (an irrelevant antibody).

That the synergy effect between a sub-toxic concentration of catalase inhibitor and an NO modulator really reflects on a synergy effect in the catalase inactivation is shown in FIG. 21. In this experiment in turn there is a peroxynitrite challenge after pre-treatment with certain active ingredients. The subsequently starting apoptosis indicates the extent of the catalase inactivation. It can be seen that the chosen salicylic acid concentration alone entails almost no catalase inactivation, but the combination of salicylic acid with taxol drastically increases its effect. This ensures that the inactivation of the catalase represents an assured biochemical consequence of the presently represented synergy system.

Figure 23:
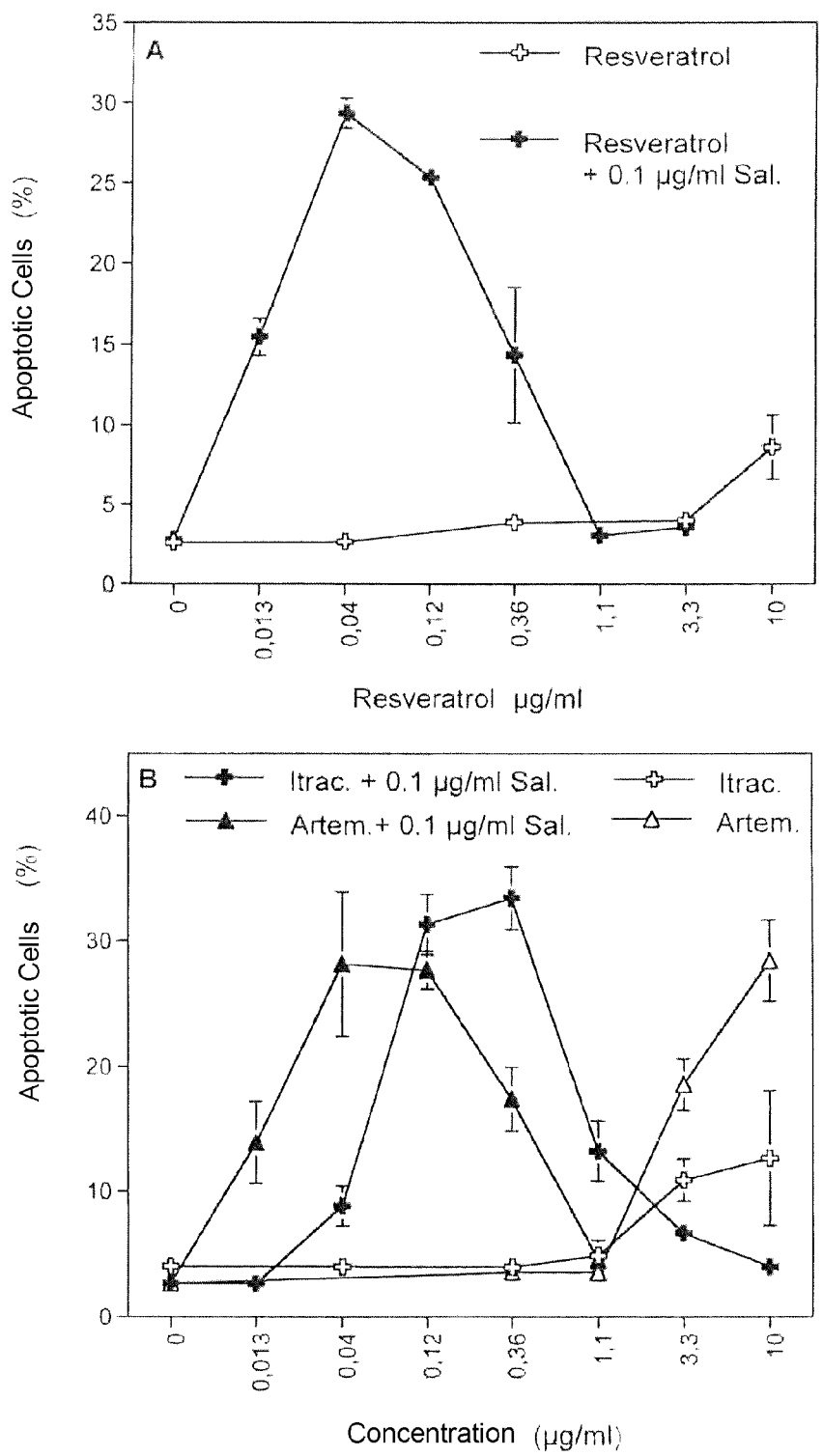
Figure 24:
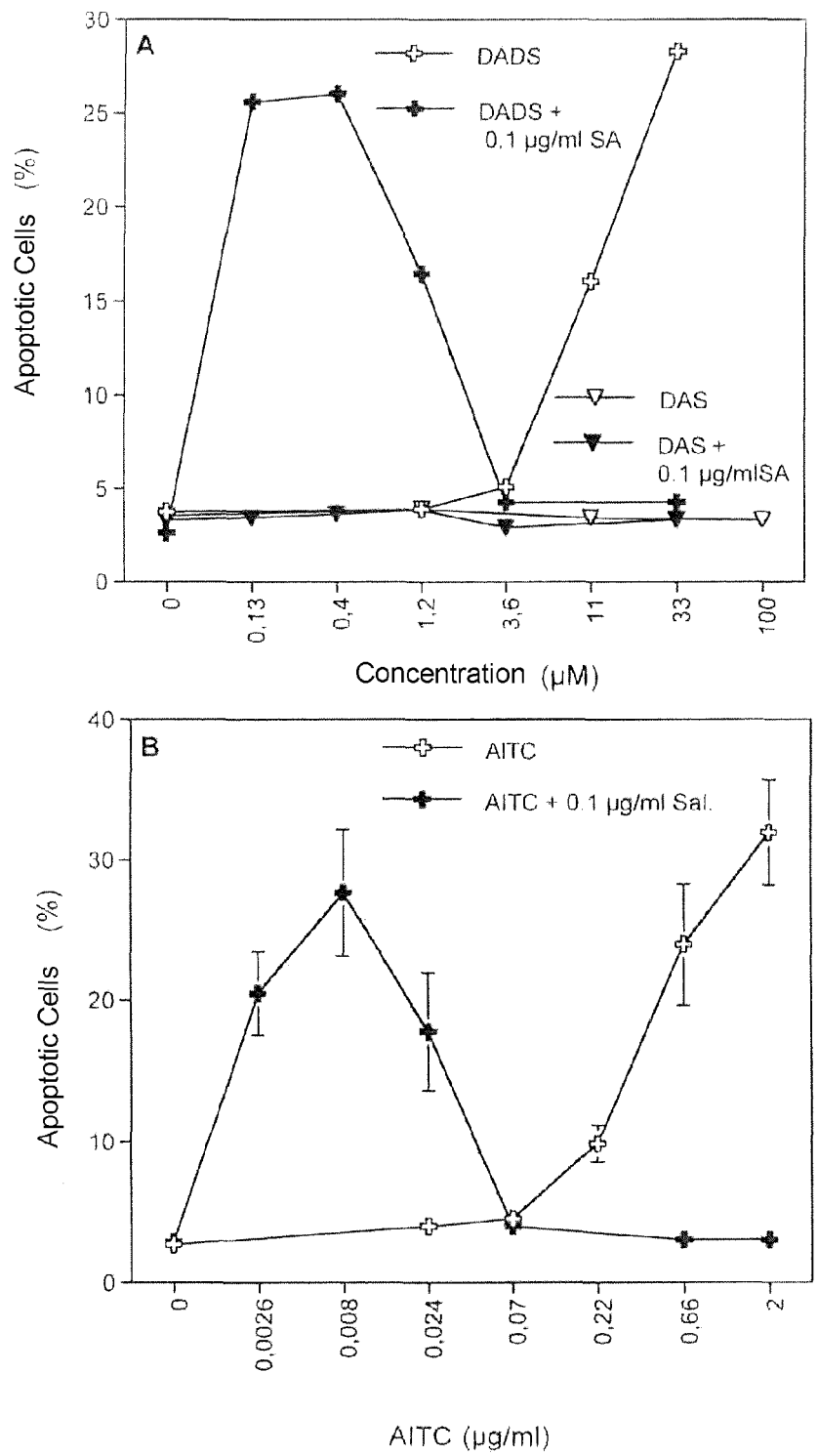

The universality of the synergistic effect between a direct catalase inhibitor (here, exemplary salicylic acid) and modulators of various ROS relevant signaling paths is illustrated in the following FIGS. 22-25. There is shown synergy between salicylic acid and arginine or arginase (ill. 17), two substances that are directly involved in the availability of NO by providing NO synthase with more substrate. The synergy effect between resveratrol, a stimulator of the NADPH oxidase, and salicylic acid is particularly impressive (FIG. 23A). At the chosen time of observation the administration of resveratrol alone still does not lead to a significant induction of apoptosis, but the combination with a sub-toxic concentration of salicylic acid enables a very strong induction of apoptosis. There are synergy effects between salicylic acid and inhibitors of the NOD such as itraconazole or artemisinin (FIG. 23B), diallyldisulfide (but not diallylsulfide) or allylisothiocyanate (FIG. 24), palmitic acid, quercetin, xanthohumol and isoxanthohumol (FIG. 25).

1.3 Model Experiments for Clearing Up the Unexpected Synergistic Interaction Between Direct Catalase Inhibitors and Modulators of the NO and Superoxide Anion Metabolism, Respectively, that Lead to an Inactivation of Catalase Due to the data present before this application it could be assumed that in parallel preformed direct catalase inhibition and inactivation of the catalase by singlet oxygen that forms after modulation of the NO or superoxide anion metabolism should only additively reinforce in their effect. So, it was also not to be expected that the presence of a lower concentration of a direct catalase inhibitor that itself does not exhibit a measurable effect in the studied system causes a noticeable increase in the effect of a modulator that inactivates catalase by the formation of singlet oxygen. However, the examples cited in this application show the opposite of this expectation.

Since the signaling processes on the membrane of individual cells cannot readily analytically be clarified a model system was used to clear up the underlying facts wherein a defined portion of the tumor cell population was bereaved of its protective catalase, the remaining portion of the population has full protection by catalase. Removal of the protective catalase was achieved by siRNA-mediated knockdown of the catalase, as described in Heinzelmann and Bauer 2010.

At first, FIGS. 26-29 show that, as expected, the pure population of control tumor cells does not go into apoptosis, while the pure population of catalase-negative tumor cells is driven to apoptosis by ROS signaling. When mixing a low percentage of catalase-negative tumor cells with untreated tumor cells this population after a certain time lag behaves as if the majority of the cells would not be protected by catalase. That is, starting from the few catalase-negative cells there must have been an inactivation of the catalase of the adjacent cells. This "quasi-infectious" or "bystander" process, as the inhibitor data show, is caused by singlet oxygen that in turn derives from peroxynitrite and hydrogen peroxide.

That is, a Locally Present Catalase Inhibition Accelerates the Singlet Oxygen Formation and Catalase Inactivation in its Cellular Environment.

It is obvious that this model established for the interaction of cells can also be applied to individual cells that imaginarily can be separated in regions with intact and inactivated catalase. Thus, the synergy effect shown in the examples of this application can be explained as follows:

Catalase of the tumor cells by efficiently decomposing hydrogen peroxide and peroxynitrite prevents both intercellular ROS signaling and singlet oxygen formation. After an increase in the available NO concentration, e.g. by an NOD inhibitor, there is transiently the singlet oxygen formation that leads to the subsequent increase in the superoxide anion production via FAS activation. This amplification step manifests in an increased singlet oxygen formation so that finally a sufficiently large number of protective catalase molecules is inactivated and apoptotic ROS signaling can run. In the presence of low concentrations of a direct catalase inhibitor the initial singlet oxygen formation is significantly made easier and thus, the inactivation of the catalase is achieved more rapid. The synergistically effective low concentration of the direct catalase inhibitor figuratively acts like a fire accelerant or a glow plug in a diesel engine. The acceleration and increase in the efficiency of the overall operation can in particular be seen in the fact that with a synergistic effect between a direct catalase inhibitor and e.g. an NOD inhibitor an enhancement of the process by the FAS receptor/Caspase-8 is no longer required, while the effect of the NOD inhibitor alone requires this enhancement.

The invention claimed is:

1. A pharmaceutical composition for the treatment of a tumor disease via the induction of selective apoptosis in tumor cells associated with said tumor disease in a subject in need thereof, said composition comprising (a) an amount of a first active ingredient that is effective to bring about a singlet oxygen-independent direct catalase inactivation, wherein said first active ingredient is selected from the group consisting of: (i) human or humanized antibodies capable of binding to membranous human catalase and (ii) human or humanized antibodies capable of binding to human superoxide dismutase, and (b) an amount of a second active ingredient that is effective to inactivate catalase through modulation of the nitrogen oxide or superoxide anion metabolism of the cells and subsequent singlet oxygen formation, wherein said second active ingredient is selected from the group consisting of: taxol, an anthocyanin, and diallyldisulfide, and combinations thereof.

2. The pharmaceutical composition according to claim 1, wherein the first active ingredient (a) is a human or humanized antibody capable of binding to membranous human catalase and the second active ingredient is taxol.

3. The pharmaceutical composition according to claim 1, wherein the first active ingredient is a human or humanized antibody capable of binding to membranous human catalase and the second active ingredient (b) is an anthocyane.

4. The pharmaceutical composition according to claim 1, wherein the first active ingredient (a) is a human or humanized antibody capable of binding to membranous human catalase and the second active ingredient (b) is diallyldisulfide.

5. The pharmaceutical composition according to claim 1, wherein the composition further comprises resveratrol.

6. A method of treating a tumor disease via the induction of selective apoptosis in tumor cells associated with said tumor disease in a subject in need thereof comprising the step of administering to said subject an effective amount of the pharmaceutical composition of claim 1.

7. The method according to claim 6, wherein the tumor disease is selected from gastric carcinoma and/or lymphoma.

* * * * *